US008383392B2

(12) United States Patent
Sumida et al.

(10) Patent No.: US 8,383,392 B2
(45) Date of Patent: Feb. 26, 2013

(54) TRANSFORMANT AND METHOD FOR PRODUCTION OF NON-NATURAL ANTIBIOTIC

(75) Inventors: Naomi Sumida, Odawara (JP); Manabu Watanabe, Odawara (JP); Koji Yanai, Odawara (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 242 days.

(21) Appl. No.: 12/678,101

(22) PCT Filed: Sep. 12, 2008

(86) PCT No.: PCT/JP2008/066596
§ 371 (c)(1),
(2), (4) Date: Mar. 12, 2010

(87) PCT Pub. No.: WO2009/035107
PCT Pub. Date: Mar. 19, 2009

(65) Prior Publication Data
US 2010/0255543 A1    Oct. 7, 2010

(30) Foreign Application Priority Data

Sep. 14, 2007   (JP) ................................ 2007-239001

(51) Int. Cl.
C12N 1/15    (2006.01)
C12P 29/00   (2006.01)
(52) U.S. Cl. ........................................ 435/254.1; 435/64
(58) Field of Classification Search .................. None
See application file for complete search history.

(56) References Cited

U.S. PATENT DOCUMENTS
4,013,515 A * 3/1977 Florent et al. .................... 435/78

FOREIGN PATENT DOCUMENTS
JP   2002-512784 A    5/2002
JP   2007-261976 A   10/2007
WO     99/55829 A1  11/1999
WO  2006/111561 A1  10/2006

OTHER PUBLICATIONS

GenEmbl database Acc#27753570 from Onaka,H. Biosynthesis of heterocyclic antibiotics in actinomycetes and an approach to synthesize the natural compounds. Actinomycetologica 20, 62-71 (2006). Alignment with SEQ Id No. 1 &2.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Krishnamurthy Madduri, et al., "Production of the antitumor drug epirubicin (4'-epidoxorubicin) and its precursor by a genetically engineered strain of *Streptomyces peucetius*)," National Biotechnology, Jan. 1998, pp. 69-74, vol. 16, No. 1.
Huawei Chen, et al., "Deoxysugars in Glycopeptide Antibiotics: Enzymatic Synthesis of TDP-L-Epivancosamine in Chloroeremomycin Biosynthesis," Proc. Natl. Acad. Sci. U.S.A., 2000, pp. 11942-11947, vol. 97, No. 22.
C.R. Hutchinson, et.al., "Genetic Engineering of Doxorubicin Production in *Streptomyces peucetius*," J. Ind. Microbiol. Biotechnol., 1999, pp. 647-652,vol. 23, No. 1.
Ke Shang, et.al., "Production of 4'-Epidaunorubicin by Metabolic Engineering of *Streptomyces coeruleorubidus* Strain SIPI-1482," World J. Microbiol. Biotechnol., Jul. 2008, pp. 1107-1113, vol. 24, No. 7.
Thomas Schmitt-John, et al., "Promoter constructions for efficient secretion expression in *Streptomyces lividans*," Appl. Microbiol. Biotechnol., 1992, pp. 493-498, vol. 36.
Mervyn J. Bibb, et al., "The mRNA for the 23S rRNA methylase encoded by the *ermE* gene of *Saccharopolyspora erythraea* is translated in the absence of a conventional ribosome-binding site," Molecular Microbiology, 1994, pp. 533-545, vol. 14, No. 3.
Practical *Streptomyces* Genetics, "Gene disruption and gene replacement," The Johns Innes Foundation, (United Kingdom), Norwick, 2000, pp. 311-338, Chapter 14.
Sharee L. Otten, et al., "Cloning and Characterization of the *Streptomyces peucetius dnmZUV* Genes Encoding Three Enzymes Required for Biosynthesis of the Daunorubicin Precursor Thymidine Diphospho-L-Daunosamine," Journal of Bacteriology, Jul. 1997, pp. 4446-4450, vol. 179, No. 13.
M. Bierman, et al., "Plasmid cloning vectors for the conjugal transfer of DNA from *Escherichia coli* to *Streptomyces* spp," Gene, 1992, pp. 43-49, vol. 116.
Tadazumi Komiyama, et al., "Baumycins, New Antitumor Antibiotics related to Daunomycin," The Journal of Antibiotics, 1977, pp. 619-621, vol. 30.
B. K. Leskiw, et al., "TTA condons in some genes prevent their expression in a class of developmental antibiotic-negative, *Streptomyces* mutants," Genetics, Proc. Natl. Acad. Sci. USA, Mar. 1991, pp. 2461-2465, vol. 88.
Wageningen Van A M A et al; Sequencing and analysis of genes involved in the biosynthesis of a vancomycin group antibiotic; Chemistry and Biology, current Biology, Londong, GB, vol. 5, No. 3, Jan. 1, 1998, pp. 155-162; XP-000915583.

\* cited by examiner

*Primary Examiner* — Sheridan Swope
(74) *Attorney, Agent, or Firm* — Sughrue Mion, PLLC

(57) ABSTRACT

Disclosed is a transformant prepared by introducing a ketoreductase gene involved in the biosynthesis of L-epivancosamine into an actinobacterium originally capable of producing daunorubicin. Also disclosed is a process of efficiently producing a non-natural daunorubicin derivative using the transformant. The transformant is capable of efficiently producing a non-natural daunorubicin derivative such as epi-daunorubicin.

4 Claims, No Drawings ment No. PCT/JP2008/066596 filed Sep. 12, 2008, claiming
TRANSFORMANT AND METHOD FOR PRODUCTION OF NON-NATURAL ANTIBIOTIC

CROSS REFERENCE TO RELATED APPLICATION

This application is a National Stage of International Application No. PCT/JP2008/066596 filed Sep. 12, 2008, claiming priority based on Japanese Patent Application No. 2007-239001, filed Sep. 14, 2007, the contents of all of which are incorporated herein by reference in their entirety.

TECHNICAL FIELD

The present invention relates to a microbial fermentation process of semi-synthetically producing a derivative of daunorubicin.

BACKGROUND ART

Anthracyclin antibiotics are a class of aromatic polyketides, and are pigment glycosides composed of an aglycon moiety, of which the basic skeleton is 7,8,9,10-tetrahydro-5,12-naphthacenequinone with the following chemical formula, and a sugar moiety, which is mainly composed of amino sugar(s).

[Chem. 1]

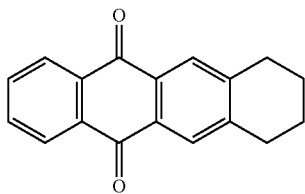

Anthracyclin antibiotics bind with DNA and generate radicals, which cleave the DNA strands or inhibit topoisomerase II. Topoisomerase has a DNase activity and a ligase activity, and catalyzes the transient cleavage of DNA strands and the religation thereof. Anthracyclin antibiotics damage DNA replication by inhibiting topoisomerase II, and exert their antitumor activity. The anthracyclin antibiotics have accumulated cardiac toxicity, but are considered to be an effective antitumor drug because of their wide spectrum of antitumor activity.

Anthracyclin antitumor drugs that are currently used include compounds, such as daunorubicin, which are derived from fermentation products, and semi-synthetic products such as doxorubicin or epirubicin, which are produced from daunorubicin as a starting material.

[Chem. 2]

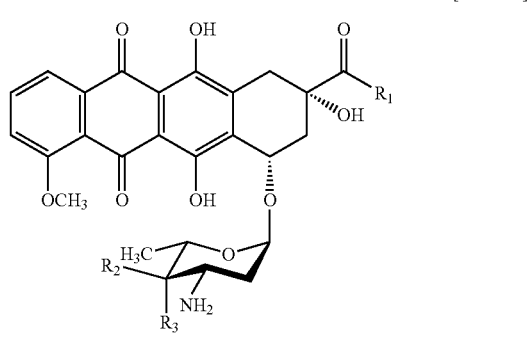

TABLE 1

|  | R1 | R2 | R3 |
| --- | --- | --- | --- |
| Daunorubicin | CH$_3$ | H | OH |
| Doxorubicin | CH$_2$OH | H | OH |
| Epidaunorubicin | CH$_3$ | OH | H |
| Epirubicin | CH$_2$OH | OH | H |

Epirubicin is superior to daunorubicin and doxorubicin in antitumor activity and toxicity, but has disadvantages in production cost. This is because epirubicin is produced from daunorubicin as a starting material, but the process includes a chemical synthesis step of reversing the hydroxyl group at 4-position of the amino sugar moiety with a low yield.

It was reported that a gene encoding a ketoreductase (epi-type ketoreductase), different in the stereospecificity of products from a ketoreductase involved in the biosynthesis of daunorubicin, was introduced into a daunorubicin-producing bacterium, and the biosynthesis pathway of daunorubicin was modified to produce epidaunorubicin by direct fermentation (non-patent literature 1). Epidaunorubicin has the same conformation of the hydroxyl group of the amino sugar moiety as epirubicin, and thus, epidaunorubicin can be used as an extremely useful starting material for the production of epirubicin. It was reported that when the epi-type ketoreductase gene (avrE) involved in the biosynthesis of avermectin was introduced, the transformant produced the largest amount of epidaunorubicin. However, the amount produced was only approximately 54 μg/mL, which did not reach a practically usefule level.

Further, a patent application in which the epidaunorubicin-producing bacterium obtained in non-patent literature 1 was treated with a mutagen to increase the productivity of epidaunorubicin to 100 μg/mL or more was filed (patent literature 1), but the obtained mutant was not described in detail in the Examples.

[patent literature 1] International Publication No. WO 2006/111561 A1
[non-patent literature 1] Madduri, K. et al., Nature Biotechnology, (U.S.A.), 1998, vol. 16, p. 69-74

DISCLOSURE OF THE INVENTION

Problems to be Solved by the Invention

An object of the present invention is to create a microorganism capable of effectively producing non-natural derivatives of daunorubicin such as epidaunorubicin.

Means for Solving the Problems

The present inventors paid attention to a possibility that the substrate specificity of each enzyme encoded by an epi-type ketoreductase gene incorporated into a host affects the productivity of a daunorubicin derivative, and compared and evaluated epi-type ketoreductase genes derived from various actinobacteria. Surprisingly, the present inventors found that a transformant into which an epi-type ketoreductase gene involved in the biosynthesis of L-epivancosamine was introduced produced three times as much epidaunorubicin as a transformant into which the avrE gene was introduced, and completed the present invention.

The present invention provides a transformant having an increased productivity of daunorubicin derivatives, i.e., the transformant into which an epi-type ketoreductase gene involved in the biosynthesis of L-epivancosamine is introduced. Further, the present invention provides a process of producing a derivative of daunorubicin, comprising the steps of cultivating the transformant of the present invention, and collecting the daunorubicin derivative from the resulting culture broth. Furthermore, the present invention provides daunorubicin derivatives produced by the transformant of the present invention.

The present invention provides the following:
(1) A transformant prepared by introducing a ketoreductase gene involved in the biosynthesis of L-epivancosamine into an actinobacterium originally capable of producing daunorubicin.
(2) The transformant of (1), which produces epidaunorubicin as a derivative of daunorubicin.
(3) The transformant of (1) or (2), wherein the ketoreductase gene involved in the biosynthesis of L-epivancosamine is
a gene which encodes a protein comprising the amino acid sequence of SEQ ID NO: 1;
a gene which encodes a protein having ketoreductase activity and comprising an amino acid sequence in which one or several amino acids are deleted, substituted, or added in the amino acid sequence of SEQ ID NO: 1; or
a gene which encodes a protein having ketoreductase activity and comprising an amino acid sequence having a 90% or more identity with the amino acid sequence of SEQ ID NO: 1.
(4) The transformant of (1) or (2), wherein the ketoreductase gene involved in the biosynthesis of L-epivancosamine is
a) a DNA consisting of the nucleotide sequence of SEQ ID NO: 2; or
b) a DNA which encodes a protein having ketoreductase activity, and hybridizes under stringent conditions to a DNA consisting of the nucleotide sequence complementary to the nucleotide sequence of SEQ ID NO: 2.
(5) The transformant of (1) to (4), wherein the host actinobacterium is *Streptomyces coeruleorubidus*.
(6) A process of producing a derivative of daunorubicin, comprising the steps of:
cultivating the transformant described in (1) to (5), and collecting the derivative of daunorubicin from the resulting culture broth.

Effects of the Invention

The transformant of the present invention may be prepared by using as a host a microorganism originally capable of producing daunorubicin, preferably actinobacteria. Known actinobacteria capable of producing daunorubicin include, for example, *Streptomyces peuceticus* and *Streptomyces coeruleorubidus*, and these microorganisms may be used as the host for preparing the transformant of the present invention. Further, actinobacteria capable of producing baumycin may be used as the host, because baumycin is a substance in which the amino sugar moiety (L-daunosamine) of daunorubicin is modified, and daunorubicin is an intermediate of the biosynthesis of baumycin. As these daunorubicin- or baumycin-producing microorganisms, a strain deficient in producing daunorubicin in which a ketoreductase gene involved in the biosynthesis of the hydroxyl group at 4-position of the L-daunosamine moiety of daunorubicin is deleted is preferably used.

The gene introduced into the host is preferably a gene encoding an epi-type ketoreductase involved in the biosynthesis of the hydroxyl group at 4-position of L-epivancosamine or a derivative thereof. L-Epivancosamine is an amino sugar which occurs naturally as part of chloroeremomycin, an antibiotic from actinobacteria, and an epi-type ketoreductase gene [Chen, H. et al., Proceedings of the National Academy of Sciences of the United States of America, (U.S.A.), 2000, vol. 97, p. 11942-11947 (non-patent literature 2)] contained in chloroeremomycin biosynthesis genes may be used in the present invention. An example of reactions in which the epi-type ketoreductase gene is involved is shown as follows:

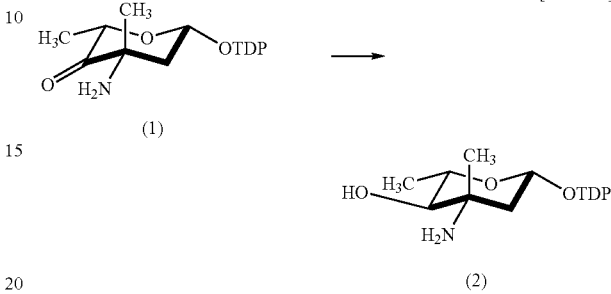

[Chem. 3]

In this reaction, the oxo group at 4-position of thymidine-5'-diphospho(TDP)-4-keto-L-vancosamine [compound (1)] is converted into a hydroxyl group to generate TDP-L-epivancosamine [compound (2)].

The gene introduced into the host is preferably a gene encoding the amino acid sequence of SEQ ID NO: 1, and more preferably a gene consisting of a DNA consisting of the nucleotide sequence of SEQ ID NO: 2. An epi-type ketoreductase gene which may be used in the present invention can be isolated by preparing a genomic DNA library of a microorganism capable of producing secondary metabolites containing L-epivancosamine (such as chloroeremomycin), and carrying out hybridization using as a probe the DNA consisting of the nucleotide sequence of SEQ ID NO: 2. Alternatively, without such a specification of the microorganism capable of producing secondary metabolites containing L-epivancosamine, a library may be prepared using DNAs directly extracted from environmental samples such as soil, and an epi-type ketoreductase gene which may be used in the present invention can be isolated in a similar fashion. The hybridization is preferably carried out under stringent conditions. The term "under stringent conditions" as used herein means the step for washing the membrane after the hybridization step is carried out at a high temperature using a washing solution having a low-salt concentration, for example, washing conditions at 60° C. for 20 minutes in a 2×SSC solution (1×SSC: 15 mmol/L trisodium citrate, 150 mmol/L NaCl) containing 0.5% SDS.

Plasmid pEVA118 comprising the DNA consisting of the nucleotide sequence of SEQ ID NO: 2 was internationally deposited, as an *Escherichia coli* transformant comprising the plasmid, in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Aug. 14, 2007, and the international deposit number is FERM BP-10898.

As the gene introduced into the host, a gene encoding a protein consisting of an amino acid sequence substantially equivalent to that of SEQ ID NO: 1 may be used. Examples of such a gene include:
a gene encoding a protein having ketoreductase activity and comprising the amino acid sequence of SEQ ID NO: 1;
a gene which encodes a protein having ketoreductase activity and comprising an amino acid sequence in which one or several amino acids are deleted, substituted, or added in the amino acid sequence of SEQ ID NO: 1; and a gene which encodes a protein having ketoreductase activity and comprising an amino acid sequence having a 90% or more identity with the amino acid sequence of SEQ ID NO: 1.

The term "ketoreductase activity" as used herein means a ketoreductase activity to convert the oxo group at 4-position of 4-keto-L-vancosamine or a derivative thereof [for example, compound (1) in the above-mentioned reaction formula] into a hydroxyl group (epi-type).

The number of amino acids modified such as "deleted, substituted, or added" is not particularly limited, so long as the ketoreductase activity is not affected. The number is, for example, 1 to 20, preferably 1 to 10, more preferably 1 to 5, and most preferably 1 to 3.

An example of modification which does not affect the activity is conservative substitution. The term "conservative substitution" as used herein means that one or plural amino acid residues contained in a polypeptide are replaced with different amino acids having similar chemical properties so that the activities of the polypeptide are not substantially changed. As the conservative substitution, there may be mentioned, for example, a substitution of a hydrophobic residue for another hydrophobic residue, or a substitution of a polar residue for another polar residue having the same charge. Amino acids which have similar chemical properties and can be conservatively substituted with each other are known to those skilled in the art. More particularly, examples of nonpolar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of basic amino acids having a positive charge include arginine, histidine, and lysine. Examples of acidic amino acids having a negative charge include aspartic acid and glutamic acid.

Examples of the gene which may be used in the present invention include a gene which encodes a protein having ketoreductase activity and comprising an amino acid sequence having a 90% or more identity (preferably a 95% or more identity, more preferably a 98% or more identity, and most preferably a 99% or more identity) with the amino acid sequence of SEQ ID NO: 1.

The term "identity" as used herein is shown as the value calculated by FASTA3 [Science, 227, 1435-1441 (1985); Proc. Natl. Acad. Sci. USA, 85, 2444-2448 (1988); and ddbj.nig.ac.jp/E-mail/homology-j.html], a known homology search program, in accordance with default parameters.

The gene may be introduced into the host by a conventional method, for example, a method of mixing protoplasts with the desired DNA, a method utilizing a phage, or a method utilizing conjugal transfer. These methods may be appropriately selected in accordance with the properties of the host. To select strains into which the epi-type ketoreductase gene of interest is introduced, it is preferable that the gene is introduced together with a vector comprising a selective marker. The selective marker is not particularly limited, so long as strains into which the epi-type ketoreductase gene is introduced can be selected. Preferred selective markers include a kanamycin resistance gene, a streptomycin resistance gene, a hygromycin resistance gene, a viomycin resistance gene, and an apramycin resistance gene. It is preferable that a promoter sequence which functions in the host is added to the epi-type ketoreductase gene to be introduced, and examples of a preferred promoter include an ermE* promoter derived from an erythromycin resistance gene [Schmitt-John, T. and Engels, J. W., Applied Microbiology and Biotechnology, (Germany), 1992, vol. 36, p. 493-498 (non-patent literature 3); and Bibb, M. J. et al., Molecular Microbiology, (United Kingdom), 1994, vol. 14, p. 533-545 (non-patent literature 4)]. The state of the epi-type ketoreductase gene introduced into the host is not particularly limited. For example, the gene may be introduced into a plasmid which can extrachromosomally self-duplicate, or into a chromosome, or may be introduced into the host by replacing the epi-type ketoreductase gene with a ketoreductase gene of the host involved in the biosynthesis of the hydroxyl group at 4-position of the L-daunosamine moiety of daunorubicin. The replacement of the gene may be carried out utilizing a method which is conventionally used for actinobacteria [Practical Streptomyces Genetics, The John Innes Foundation, (United Kingdom), Norwich, 2000, p. 311-338 (non-patent literature 5)].

Daunorubicin derivatives produced by the transformant of the present invention are daunorubicin derivatives in which the hydroxyl group at 4-position of the L-daunosamine moiety of daunorubicin is reversed, preferably epidaunorubicin or epirubicin, and more preferably epidaunorubicin.

The transformant of the present invention may be cultivated in accordance with a conventional method to produce the daunorubicin derivatives, using a medium including conventional components. As carbon sources, for example, glucose, sucrose, syrup, dextrin, starch, glycerol, molasses, animal oils, or vegetable oils may be used. As nitrogen sources, soybean meal, wheat germ, corn steep liquor, cotton seed meal, meat extract, polypeptone, malt extract, yeast extract, ammonium sulfate, sodium nitrate, or urea may be used. If desired, it is preferable that inorganic salts capable of generating sodium, potassium, calcium, magnesium, cobalt, chlorine, phosphoric acid (such as dipotassium hydrogen phosphate), sulfuric acid (such as magnesium sulfate), or other ions may be supplemented. Further, if desired, thiamine (such as thiamine hydrochloride) or other vitamins; glutamic acid (such as sodium glutamate), asparagine (such as DL-asparagine), or other amino acids; nucleotides or other micronutrients; or antibiotics or other selection agents may be supplemented. Furthermore, organic or inorganic substances capable of promoting the growth of the transformant and the production of the daunorubicin derivatives may be appropriately added.

The pH of the medium is, for example, approximately 5.5 to 8. The cultivation may be carried out by a solid cultivation under aerobic conditions, a shaking cultivation, an agitating cultivation with aeration, or a submerged cultivation with aeration, and most preferably a submerged cultivation with aeration. Appropriate temperatures for cultivation are 15° C. to 40° C., and the transformant can grow at approximately 25° C. to 35° C. in almost all cases. The production of the daunorubicin derivatives varies in accordance with the medium, cultivation conditions, or the type of the host, but the accumulation of the products generally reaches its maximum after 2 to 10 days in any cultivation. When the amounts of the daunorubicin derivatives reach the maximum during the cultivation, the cultivation is stopped, and the desired products are isolated and purified from the resulting culture.

To collect the daunorubicin derivatives from the culture obtained by cultivating the transformant of the present invention, the extraction and purification thereof from the culture can be carried out using a conventional separation method, which may be selected in accordance with their properties, for example, solvent extraction, an ion exchange resin method, adsorption or partition column chromatography, gel filtration, dialysis, precipitation, or crystallization alone, or an appropriate combination thereof. The resulting daunorubicin derivatives can be further purified by chromatography using an adsorbing agent such as silica gel or alumina, Sephadex LH-20 (manufactured by Pharmacia), or TOYOPEARL HW-40 (manufactured by TOSOH Corporation).

The present invention now will be further illustrated by, but is by no means limited to, the following Examples. Various changes and modifications are possible without departing from the scope of the appended claims.

EXAMPLE 1

Cloning of Ketoreductase Gene Contained in Daunorubicin Biosynthesis Genes in *Streptomyces Coeruleorubidus*

*Streptomyces coeruleorubidus* was inoculated in 50 mL of a modified YEME medium (0.3% Difco yeast extract, 0.5% Difco bacto peptone, 0.3% oxoid malt extract, 1% glucose, 3% sucrose, 5 mmol/L $MgCl_2 \cdot 6H_2O$), and cultivated at 28° C. for 24 hours while shaking at 220 rpm. The resulting culture broth was centrifuged at 6300×g for 10 minutes, and the supernatant was decanted to collect the mycelia. The collected mycelia were lyophilized, and genomic DNA was prepared using ISOPLANT (manufactured by Nippon Gene Co., Ltd.) in accordance with a protocol attached thereto.

The genomic DNA was partially digested with Sau3AI, and subjected to low melting point agarose gel electrophoresis to collect DNA fragments of 9 to 23 kbp by a conventional method. The collected DNA fragments were ligated with a phage vector using a phage vector EMBL3/BamHI vector kit (manufactured by Stratagene) and a DNA ligation kit ver.2 (manufactured by Takara Shuzo Co., Ltd.), and in vitro packaging was carried out using MaxPlax lambda packaging extracts (manufactured by EPICENTRE Biotechnologies). The resulting recombinant phages were infected to E. coli XL1-Blue MRA (P2), and plaques were formed on plates to prepare genomic DNA libraries.

A probe for screening the genomic DNA libraries was prepared as described follows. Genomic DNA was prepared from Streptomyces peucetius ATCC 29050 in accordance with the above-mentioned method. To amplify a dnmV gene [Otten, S. L. et al., Journal of Bacteriology, (U.S.A.), 1997, vol. 179, p. 4446-4450 (non-patent literature 6)] encoding 4-ketoreductase by a PCR method using this genomic DNA as the template, the following synthetic oligonucleotides were synthesized.

```
SP-dnmV N:
5'-ATGCGGGTCGTGGTTCTGGG-3'    (SEQ ID NO: 3)

SP-dnmV C:
5'-CTAGGCCGGGGCGCCGTGCG-3'    (SEQ ID NO: 4)
```

This PCR was carried out using approximately 1 pg of genomic DNA and 1 pmol/L each primer, together with an LA Taq DNA polymerase (manufactured by Takara Shuzo Co., Ltd.), under the following cycle conditions:

a reaction at 94° C. for 5 minutes was carried out;

a cycle consisting of a reaction at 94° C. for 30 seconds, a reaction at 48° C. for 30 seconds, and a reaction at 72° C. for 1 minute was repeated 25 times; and a reaction at 72° C. for 7 minutes was carried out. As a result, a DNA fragment of approximately 0.9 kbp was specifically amplified. It was confirmed that this DNA fragment was the dnmV gene of interest by determining the nucleotide sequence of the DNA fragment. This DNA fragment was used as a probe in the following procedure.

The genomic DNA libraries were screened using an ECL direct DNA/RNA labeling detection system (manufactured by Amersham Pharmacia Biotech). In accordance with a protocol attached thereto, 100 ng of the DNA fragment of approximately 0.9 kbp was labeled. The genomic DNA libraries were screened by plaque hybridization using the labeled probe to obtain three positive clones.

Phage DNAs were isolated and purified from these clones, and the nucleotide sequence (SEQ ID NO: 5) of 7330 by around the region to which the probe hybridized was determined. As a result, it was confirmed that this nucleotide sequence showed a high homology with those of known daunorubicin biosynthesis genes, and contained the dmnV gene encoding ketoreductase involved in the biosynthesis of daunorubicin in *Streptomyces coeruleorubidus*.

EXAMPLE 2

Construction of Plasmid pDDNMV for Gene Disruption of dnmV Gene in *Streptomyces Coeruleorubidus*

To disrupt the dnmV gene by inserting a stop codon midway of its coding region, a DNA fragment containing a dnmV gene into which a stop codon was inserted was prepared by a two-step PCR method using, as the template, the DNA fragment isolated in Example 1. As the primers, primers containing a HindIII or XbaI recognition site, and a primer into which a stop codon TAG was inserted at the 84th tyrosine site (TAC) from the initiation codon of the dnmV gene were designed.

```
Dau5-HindIII:
                               (SEQ ID NO: 7)
5'-GGGAAGCTTGATCGCCCTCACGGAACTGCGCAGGCGCGG-3' dnmV-84Yc:
                               (SEQ ID NO: 8)
5'-CGCAGATGCGACTACGTCATCTCC-3'
(the stop codon is underlined, SEQ ID NO: 8)

Dau3-XbaI:
                               (SEQ ID NO: 9)
5'-GGGTCTAGAGCCGGCATGCGGATCGGCATGGAGGTG-3'
```

The PCR reaction in the first step was carried out in 50 µL of a reaction solution using the Dau5-HindIII primer (0.3 µmol/L), the dnmV-84Yc primer (0.3 µmol/L), and the template DNA (1 µg), together with a KOD Plus DNA polymerase (manufactured by TOYOBO Co., Ltd.), under the following cycle conditions:

a reaction at 94° C. for 2 minutes was carried out; and a cycle consisting of a reaction at 94° C. for 15 seconds, a reaction at 50° C. for 30 seconds, and a reaction at 68° C. for 1 minute and 30 seconds was repeated 25 times.

The resulting PCR reaction product was purified using a High Pure PCR Product Purification Kit (manufactured by Roche) to obtain 50 µL of a DNA solution. From the resulting DNA solution, 20 µL thereof was used as a primer for the PCR reaction in the second step. This PCR reaction was carried out in 50 µL of a reaction solution using the Dau3-XbaI primer (0.3 µmol/L) as another primer and the template DNA (1 µg), together with a KOD Plus DNA polymerase (manufactured by TOYOBO Co., Ltd.), under the following cycle conditions:

a reaction at 94° C. for 2 minutes was carried out; and a cycle consisting of a reaction at 94° C. for 15 seconds, a reaction at 50° C. for 30 seconds, and a reaction at 68° C. for 4 minutes was repeated 25 times. As a result, a DNA fragment of approximately 3 kbp was specifically amplified. This DNA fragment was double-digested with HindIII and XbaI, and cloned between the HindIII and XbaI sites of pUC119. The nucleotide sequence of the cloned DNA fragment was determined to confirm that it was a DNA fragment containing the desired dnmV gene into which a stop codon was inserted.

Plasmid pSET152 for the conjugal transfer in actinobacteria [Bierman, M. et al., Gene, (Netherlands), 1992, vol. 116, p. 43-49 (non-patent literature 7)] was digested with SphI, blunt-ended with T4 DNA polymerase, and ligated with a HindIII linker (manufactured by Takara Shuzo Co., Ltd.) to construct pSET153. A HindIII-XbaI fragment of approximately 2.8 kbp derived from pSET153 was ligated to a HindIII-XbaI fragment of approximately 3 kbp containing the dnmV gene into which a stop codon was inserted, to construct conjugal transfer plasmid pDDNMV for gene disruption of the dnmV gene.

EXAMPLE 3

Generation of dnmV-Disrupted Strain Using Plasmid pDDNMV for Gene Disruption of dnmV Gene

*Streptomyces coeruleorubidus* capable of producing daunorubicin was inoculated on an MS agar medium (2% S soybean meal, 2% mannitol, 2% agar), and cultivated at 28° C. for 7 days. After the cultivation, spores were scraped with 3 mL of a 2×YT broth (1.6% Difco bacto tryptone, 1% Difco bacto yeast extract, 0.5% NaCl), and heat-shocked at 50° C. for 10 minutes to prepare a liquid of host spores.

*Escherichia coli* containing plasmid pDDNMV (strain ET12567/pUZ8002) was inoculated into 100 mL of an LB liquid medium (1% Difco bacto tryptone, 0.5% Difco bacto yeast extract, 0.5% NaCl, 0.1% glucose) containing 25 µg/mL chloramphenicol, 25 µg/mL kanamycin and 50 µg/mL apramycin, and cultivated at 37° C. overnight to prepare a preculture. This preculture was inoculated into the same LB liquid medium to give a final concentration of 1%, and cultivated at 37° C. for about 4 hours. After the cultivation, *E. coli* was washed with the LB liquid medium twice, and finally suspended in 10 mL of the LB liquid medium to prepare a liquid of *E. coli*.

After 500 µL of the liquid of host spores was mixed with 500 µL of the liquid of *E. coli*, the collected mixture was inoculated on an MS agar medium supplemented with $MgCl_2$ (final concentration: 10 mmol/L). After cultivation at 28° C. for 20 hours, 1 mL of sterile water containing 1 mg of apramycin and 1.5 mg of nalidixic acid was layered on the MS agar medium. Cultivation at 28° C. for 5 days was carried out to obtain apramycin-resistant strains.

Genomic DNAs were prepared from the obtained apramycin-resistant strains using an apparatus for purification of genomic DNA (MagExtractor, manufactured by TOYOBO Co., Ltd.) in accordance with a protocol attached thereto, and it was confirmed by PCR and Southern blotting that pDDNMV was inserted into the chromosomes by homologous recombination.

The homologous recombinant was inoculated into a modified YEME medium (50 mL) and cultivated at 28° C. for 2 days while shaking, and 1 mL of this culture was inoculated into a fresh modified YEME medium (50 mL) to perform subculture. After this subculture was repeated five times, the resulting culture was diluted so as to give an appropriate viable cell number, and the diluted culture was inoculated on an MS agar medium and cultivated at 28° C. for 4 days. The grown colonies were replicated on an MS agar medium containing 20 µg/mL apramycin and an MS agar medium without apramycin, to select 7 apramycin-sensitive strains which could not grow on the apramycin-containing medium.

Genomic DNAs were prepared from the selected apramycin-sensitive strains, and PCR reactions were carried out using a combination of primer Da25 (5'-ATGCTGGGCATCTACGTC-3', SEQ ID NO: 10) and primer DaBR (5'-ACCGTACTCGTGCACCGA-3', SEQ ID NO: 11) to obtain amplified DNA fragments of approximately 1.5 kbp. The nucleotide sequence of each amplified DNA fragment was determined, and as a result, 6 strains were dnmV-gene-disrupted strains into which the stop codon was inserted as designed, and 1 strain maintained the original nucleotide sequence.

To confirm the production of daunorubicin in these strains, each strain was inoculated into 40 mL of a liquid production medium [Komiyama, T. et al., The Journal of Antibiotics, (Japan), 1977, vol. 30, p. 619-621 (non-patent literature 8)] prepared in a 250-mL Erlenmeyer flask, and cultivated at 28° C. for 2 days. Further, 1 mL of each culture was inoculated into 20 mL of the same liquid production medium, and cultivated at 32° C. for 7 days. To extract products generated by each strain, 1 mL of each culture, 1 mL of methanol, and 70 µL of 50% $H_2SO_4$ were added to 15-mL Falcon centrifuge tubes, shaken for 1 hour, and centrifuged at 2000×g for 10 minutes, and the resulting supernatants were subjected to HPLC analysis. As a result, the production of daunorubicin was not observed in 6 dnmV-gene-disrupted strains, but only the strain in which the dnmV gene reverted to the original nucleotide sequence of the parent strain produced daunorubicin.

EXAMPLE 4

Expression of Ketoreductase Genes in dnmV-Gene-Disrupted Strain as Host

Plasmid pIJ4070 containing an ermE* promoter [Leskiw, B. K. et al., Proceedings of the National Academy of Sciences of the United States of America, (U.S.A.), 1991, vol. 88, p. 2461-2465 (non-patent literature 9)] was double-digested with EcoRI and BamHI, and fractionated by electrophoresis, and an EcoRI-BamHI fragment of approximately 0.3 kbp containing the ermE* promoter was extracted from the gel. This EcoRI-BamHI fragment was inserted between the EcoRI and BamHI sites of plasmid pSET152 to obtain plasmid pSET152-E*.

To isolate ketoreductase genes (orf29, eryBIV, avrE, and oleU) involved in the biosynthesis of sugars contained in antibiotics from a medemycin-producing bacterium (*Streptomyces mycarofaciens*) owned by Meiji Seika Kaisha, Ltd., an erythromycin-producing bacterium (*Saccharopolyspora erythraea*) owned by Meiji Seika Kaisha, Ltd., Streptomyces avermitilis JCM5070 as an avermectin-producing bacterium, and *Streptomyces olivocromogenes* NBRC12444 as an oleandomycin-producing bacterium, respectively, genomic DNA from each strain was used as a template to carry out a PCR using the following primers. A combination of orf29N-BglII and orf29C-XbaI for the medemycin-producing bacterium, a combination of eryBIVN-BamHI and eryBIVC-XbaI for the erythromycin-producing bacterium, a combination of avrEN-BamHI and avrEC-XbaI for the avermectin-producing bacterium, and a combination of oleUN-BamHI and oleUC-XbaI for the oleandomycin-producing bacterium, were used.

```
orf29N-BglII
                                            (SEQ ID NO: 12)
5'-GGGAGATCTAGCGAAGGAGAAGTATGAGGCTCACTACCG-3' orf29C-XbaI
                                            (SEQ ID NO: 13)
5'-GGGTCTAGATCAAGAACTCACCGCCGG-3' eryBIVN-BamHI
                                            (SEQ ID NO: 14)
5'-GGGGGATCCAGCGAAGGAGCAAAGCTCCGATGAATGGGA-3' eryBIVC-XbaI
                                            (SEQ ID NO: 15)
5'-GGGTCTAGACTAGTGCTCCTCGGTGGG-3' avrEN-BamHI
                                            (SEQ ID NO: 16)
5'-GGGGGATCCAGCGAAGGAGGGGCCACCAGATGGGG-3' avrEC-XbaI
                                            (SEQ ID NO: 17)
5'-GGGTCTAGACTACACGTAAGCCGCCAC-3' oleUN-BamHI
                                            (SEQ ID NO: 18)
5'-GGGGGATCCAGCGAAGGAGGCAGCGGCCCCATGAGATGG-3' oleUC-XbaI
                                            (SEQ ID NO: 19)
5'-GGGTCTAGATCATGCTGCTCCTCGCCGG-3'
```

Each PCR was carried out in 50 μL of a reaction solution using 0.3 μmol/L each primer and 1 μg of genomic DNA as a template, together with a KOD Plus DNA polymerase (manufactured by TOYOBO Co., Ltd.), under the following cycle conditions:

a reaction at 94° C. for 2 minutes was carried out; and a cycle consisting of a reaction at 94° C. for 10 seconds, a reaction at 50° C. for 30 seconds, and a reaction at 68° C. for 1 minute was repeated 25 times. The DNA fragments of approximately 1 kbp amplified by each PCR were double-digested with BglII and XbaI (for the DNA fragment derived from the medemycin-producing bacterium) or BamHI and XbaI (for the other DNA fragments), and inserted between the BamHI and XbaI sites of plasmid pSET152-E* to obtain plasmid pMED-E (gene derived from the medemycin-producing bacterium), plasmid pERY-E (gene derived from the erythromycin-producing bacterium), plasmid pAVR-E (gene derived from the avermectin-producing bacterium), and plasmid pOLE-E (gene derived from the oleandomycin-producing bacterium). The nucleotide sequences of the inserted sequence in these plasmids are shown as SEQ ID NOS: 20, 22, 24, and 26.

With respect to a ketoreductase gene (evaE) of a chloroeremomycin-producing bacterium (*Amycolatopsis orientalis*), the BamHI-XbaI fragment consisting of the nucleotide sequence of SEQ ID NO: 28, of which the full sequence was chemically synthesized, was inserted between the BamHI and XbaI sites of plasmid pSET152-E* to obtain plasmid pEVA-E.

An DaN-1 strain, one of the dnmV-gene-disrupted strains described in Example 3, was used as a host, and each of the five plasmids prepared above was introduced into the host by conjugal transfer. The resulting transformants were cultivated in the above-mentioned liquid production medium at 28° C. for 7 days (n=3). Extracts from each mycelium were subjected to HPLC analysis to determine the amounts of epidaunorubicin produced. As shown in Table 2, it was found that the transformant into which the ketoreductase gene derived from the chloroeremomycin-producing bacterium was introduced produced epidaunorubicin in remarkably large amounts.

TABLE 2

| Strains | Amount of epidaunorubicin produced (μg/mL) |
| --- | --- |
| DaN-1/pMED-E | 21.0 ± 1.2 |
| DaN-1/pERY-E | 9.0 ± 0.6 |
| DaN-1/pAVR-E | 63.7 ± 2.4 |
| DaN-1/pOLE-E | 9.0 ± 1.0 |
| DaN-1/pEVA-E | 173.0 ± 5.2 |
| DaN-1 | 0 |

Although the present invention has been described with reference to specific embodiments, various changes and modifications obvious to those skilled in the art are possible without departing from the scope of the appended claims.

FREE TEXT IN SEQUENCE LISTING

Features of "Artificial Sequence" are described in the numeric identifier <223> in the Sequence Listing. The nucleotide sequences of SEQ ID NOS: 3, 4, 7 to 19, and 28 are synthetic DNAs.

The invention claimed is:

1. A transformant of an actinobacterium, originally capable of producing daunorubicin, comprising a ketoreductase gene involved in the biosynthesis of L-epivancosamine, wherein the ketoreductase gene is selected from:
   a) a gene which encodes a protein comprising the amino acid sequence of SEQ ID NO: 1;
   b) a gene which encodes a protein comprising an amino acid sequence in which 1-20 amino acids are deleted, substituted, or added in the amino acid sequence of SEQ ID NO: 1 wherein said amino acid sequence has ketoreductase activity;
   c) a gene which encodes a protein comprising an amino acid sequence having a 95% or more identity with the amino acid sequence of SEQ ID NO: 1 wherein said amino acid sequence has ketoreductase activity; or
   d) a DNA consisting of the nucleotide sequence of SEQ ID NO: 2.

2. The transformant according to claim 1, which produces epidaunorubicin as the derivative of daunorubicin.

3. The transformant according to claim 1, wherein the host actinobacterium is *Streptomyces coeruleorubidus*.

4. A process of producing a derivative of daunorubicin, comprising the steps of:
   cultivating the transformant of claim 1, and
   collecting epidaunorubicin as the derivative of daunorubicin from the resulting culture broth.

* * * * *

SEQUENCE LISTING

```
<160> NUMBER OF SEQ ID NOS: 28

<210> SEQ ID NO 1
<211> LENGTH: 325
<212> TYPE: PRT
<213> ORGANISM: Amycolatopsis orientalis

<400> SEQUENCE: 1

Met Lys Leu Ile Thr Val Leu Gly Ala Ser Gly Phe Ile Gly Ser Ala
1               5                   10                  15

Val Thr Arg Ala Leu Ala Gln Gln Pro Ile Arg Leu Arg Ala Val Ala
            20                  25                  30

Arg Arg Gln Phe Thr Pro Ala Pro Gly Gln Ala Glu Thr Thr Val Val
        35                  40                  45

Ala Ala Asp Leu Thr Asp Arg Val Ala Leu Ala Asp Ala Val Ala Gly
    50                  55                  60
```

```
Ser Asp Ala Val Val Tyr Leu Leu Ser Asp Gly Gly Trp Arg Ala
 65                  70                  75                  80

Val Glu Thr Glu Asp Ala Glu Arg Val Asn Val Gly Val Met Arg Asp
                 85                  90                  95

Leu Ile Asp Val Thr Gly Ser Asp Asn Gly Thr Pro Pro Val Val Val
            100                 105                 110

Phe Gly Gly Thr Val Ser Gln Val Gly Val Pro Pro Arg Glu Pro Leu
        115                 120                 125

Asp Gly Ser Glu Pro Asp Asn Pro Ala Thr Pro Tyr Asp Ile Gln Lys
    130                 135                 140

Leu Thr Ala Glu Gln Ile Leu Lys Lys Ala Thr Ala Asn Gly Gln Val
145                 150                 155                 160

Arg Gly Ile Ser Leu Arg Leu Pro Thr Ile Phe Gly Glu Thr Thr Ala
                165                 170                 175

Gln Gly Ala Asn His Asp Arg Gly Val Val Ser Ser Met Ala Arg Arg
            180                 185                 190

Ala Leu Asp Gly Gln Ala Leu Thr Ile Trp Gly Asp Gly Ser Val Arg
        195                 200                 205

Arg Asp Val Val His Val Glu Asp Val Ala Ala Phe Thr Ala Ala
    210                 215                 220

Leu Ala Asn Pro Asp Ser Leu Val Gly Gly His Trp Leu Ile Gly Ala
225                 230                 235                 240

Gly Arg Gly Asp Gln Leu Gly Glu Ile Phe Arg Leu Val Ala Arg Glu
                245                 250                 255

Val Ala Glu Gln Thr Gly Gln Arg Pro Val Glu Val Thr Cys Val Glu
            260                 265                 270

Pro Pro Ser His Ala Pro Glu Met Asp Phe Arg Ser Val Thr Ile Asp
        275                 280                 285

Ser Ser Pro Phe Arg Ala Val Thr Gly Trp Arg Pro Glu Ile Ser Leu
    290                 295                 300

Ser Glu Gly Val Arg Arg Thr Val Ala Ala Leu Thr Thr Ser Val His
305                 310                 315                 320

Gly Lys Ala Arg Ala
                325

<210> SEQ ID NO 2
<211> LENGTH: 978
<212> TYPE: DNA
<213> ORGANISM: Amycolatopsis orientalis

<400> SEQUENCE: 2
atgaagctga tcaccgtgct cggtgcgtcg ggcttcatcg ctcggctgt cacgcgtgca      60 ctggcgcagc agccaatccg gctgcgagcg gtggcgcgca ggcagttcac gcccgcgccc     120
ggccaagccg agacgaccgt cgtcgccgct gatctcaccg accgtgtcgc gctcgccgac     180
gcggtcgcgg gatcggacgc ggtcgtgtac ctgcttctgt cagacggcgg atggcgcgcg     240
gtcgagaccg aggacgccga acgcgtgaac gtgggcgtca tgcgggacct catcgacgtc     300
accggcagcg acaacgggac gccccggtg gtggtgttcg gcggtaccgt ctcgcaggtc      360
ggtgtgccac tcgggagcc gctcgacggc agcgagcccg acaacccggc gactccctac     420
gacatacaga agctgacagc ggaacagatc ctcaagaagg ccacggcaaa tggccaggtg     480
cgcggcatca gctgcgtct gccgacgata ttcggtgaaa ccacggcaca aggcgcgaac     540
cacgaccgcg gtgtcgtgtc gtccatggcg cggcgagcgc tcgacggcca ggcactcacc     600
```

| | |
|---|---|
| atctggggcg acggcagcgt gcgacgcgac gtcgtccatg tcgaggacgt cgcggcggcg | 660 |
| ttcaccgcgg cactggccaa cccgattcc cttgtcggcg gccactggct gatcggcgcg | 720 |
| ggccgaggcg atcagcttgg ggagattttc cgcctcgtgg cacgggaagt ggccgagcag | 780 |
| accgggcagc gcccggtcga ggtgacctgt gtggaaccac cgtcgcacgc acctgagatg | 840 |
| gatttccgca gcgtcaccat cgattcctcg ccgttccggg cggtcaccgg ctggcgccca | 900 |
| gagatttcgc tgtccgaagg agtgcgtcgc actgtcgccg cattgacgac atcagttcat | 960 |
| ggaaaggctc gcgcatga | 978 |

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3

| | |
|---|---|
| atgcgggtcg tggttctggg | 20 |

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4

| | |
|---|---|
| ctaggccggg gcgccgtgcg | 20 |

<210> SEQ ID NO 5
<211> LENGTH: 7330
<212> TYPE: DNA
<213> ORGANISM: Streptomyces coeruleorubidus
<220> FEATURE:
<221> NAME/KEY: CDS
<222> LOCATION: (1069)..(1992)
<223> OTHER INFORMATION: dnmV, ketoreductase

<400> SEQUENCE: 5

| | |
|---|---|
| gatcgccctc acggaactgc gcaggcgcgg cggggcgccg gccggggtgc ggaccacggt | 60 |
| ggccgagata gacgcccggc tgttcgcgct gcacacggcg gtggcgagcg cgttgaccac | 120 |
| cgccgaccgg ctcgccgacg acctcagcgg cgacctcgcc gcccgcggcc gcgccatgat | 180 |
| gacgcccttc cagtacgcca agctgctcgt caaccggcac tcggtgggcg tggtggacga | 240 |
| ctgcctgatg ctcgtgggag gggccggata cagcaactcc cacccgctgg cgcgcctgta | 300 |
| ccgcgatgtc cgggcgggcg ggttcatgca tccgtacaac ttcacggacg cgtcgacta | 360 |
| cctgagcgaa gtggtgttgg gccgatgagc ggcgggcgac gcgggaccgg atccctgga | 420 |
| gtcggaggac gtggatgaag gcgcgggaac tggcggtgca gggggcgtac acgttcgagc | 480 |
| cggaggtgtt tccggacgag cggggggctgt tcgtctcacc gttccgggag gatgcgttca | 540 |
| cggccgcggt cggccatccg ctcttcccgg tgcggcagac gaatcacagc cggtcgcggc | 600 |
| gtggggtggt gcggggcgtg cactacaccg tgacgccgcc gggctcggcc aagtacgtgt | 660 |
| actgcgcccg tggcaggtcg ctggacatcg tcgtcgacgt gcgggtcggc tccccgacgt | 720 |
| acggccggtg ggacgccgtc gagctggagc gcgtgagtt ccgggcggtg tacttcccgg | 780 |
| tcggggtggg gcacgccttc gtggccctgg aggacgacac cgtcatgtcg tacatgctgt | 840 |

-continued

```
cagggggagta cgtgcaggcc aacgaactcg ccgtgtcggt gctggacccg ccctcgggc       900 ttcccgtgcc gggtgacctg gagcctctgc tgtccggccg ggaccgggcc gcaccgcccc       960
tggagcaggc ccgggccgcg gggacccttc cggagtacgc cgcgtgccgg cggtcgagt      1020 cggagctgtg gccgccggcc gggtcacgcg gagacgggtg aggcggac atg cgg gtc      1077
                                                   Met Arg Val
                                                    1
```

| gtg gtt ctg ggg gcg acg ggc agc gtc ggc cgg cag gtg tgt gcg gcg | 1125 |
|---|---|
| Val Val Leu Gly Ala Thr Gly Ser Val Gly Arg Gln Val Cys Ala Ala | |
| 5                 10                  15                        | |

| tac cag gcg cac ggg tgg gac gtg cac ggg gtg gcc cgc cgc ccg gcg | 1173 |
|---|---|
| Tyr Gln Ala His Gly Trp Asp Val His Gly Val Ala Arg Arg Pro Ala | |
| 20                  25                  30                  35  | |

| ccg cat ctg agc ggg tgc ggg ttc acg gag ctg gac ctc gcg gcc gcc | 1221 |
|---|---|
| Pro His Leu Ser Gly Cys Gly Phe Thr Glu Leu Asp Leu Ala Ala Ala | |
|              40                  45                  50         | |

| gcg cct ggg cgg atc gcc acg gtg ctg ggt gat ccc ccg gcg gac gtc | 1269 |
|---|---|
| Ala Pro Gly Arg Ile Ala Thr Val Leu Gly Asp Pro Pro Ala Asp Val | |
|         55                  60                  65              | |

| gtg gtc aac gcg gcg ggc ggc tgg ggc gac acc gag gag gag atg acg | 1317 |
|---|---|
| Val Val Asn Ala Ala Gly Gly Trp Gly Asp Thr Glu Glu Glu Met Thr | |
|     70                  75                  80                  | |

| tac tcg cat ctg cga ctg gtg cga cgc ctg gtg gag gcg ctc gcg ctg | 1365 |
|---|---|
| Tyr Ser His Leu Arg Leu Val Arg Arg Leu Val Glu Ala Leu Ala Leu | |
| 85                  90                  95                      | |

| ctc ccg ttc cgg ccc cgg ctg gtc cat ctg ggg tcg gtg cac gag tac | 1413 |
|---|---|
| Leu Pro Phe Arg Pro Arg Leu Val His Leu Gly Ser Val His Glu Tyr | |
| 100                 105                 110                 115 | |

| ggt ccc gtg ccg gcc ggc acg ctg ctg cac gag gac ctg ccg ccg gag | 1461 |
|---|---|
| Gly Pro Val Pro Ala Gly Thr Leu Leu His Glu Asp Leu Pro Pro Glu | |
|                 120                 125                 130     | |

| ccg gtc acg ccg tac gcg cgc gtc aaa ctg gag acc tcg tcg gcc gtc | 1509 |
|---|---|
| Pro Val Thr Pro Tyr Ala Arg Val Lys Leu Glu Thr Ser Ser Ala Val | |
|             135                 140                 145         | |

| ctg acc gcg gcg cgg gcc ggt gtc ctg gac gcg gtg gtg ctg cgc gcg | 1557 |
|---|---|
| Leu Thr Ala Ala Arg Ala Gly Val Leu Asp Ala Val Val Leu Arg Ala | |
|         150                 155                 160             | |

| gcg aac atg tcg ggc ccg cat ccg ccg cag gag agt ttc ctg gcc gcc | 1605 |
|---|---|
| Ala Asn Met Ser Gly Pro His Pro Pro Gln Glu Ser Phe Leu Ala Ala | |
| 165                 170                 175                     | |

| ctg atg gcg cgt atc agc acg gcg ttc gcg cac ggt ggg cgg ctg gag | 1653 |
|---|---|
| Leu Met Ala Arg Ile Ser Thr Ala Phe Ala His Gly Gly Arg Leu Glu | |
| 180                 185                 190                 195 | |

| ttg agc gtc gcg gac gca cgg cgg gac ttc gtc gac gtg cgg gac gtc | 1701 |
|---|---|
| Leu Ser Val Ala Asp Ala Arg Arg Asp Phe Val Asp Val Arg Asp Val | |
|                 200                 205                 210     | |

| gca cag gcg gtg gtg cgg gcc ggg cgg gct ccg gcg gtc ggc gga ctg | 1749 |
|---|---|
| Ala Gln Ala Val Val Arg Ala Gly Arg Ala Pro Ala Val Gly Gly Leu | |
|             215                 220                 225         | |

| gtc gtc aac atc ggg cgc ggg gac gcc gtg ccg atc ggt gat ctg gtc | 1797 |
|---|---|
| Val Val Asn Ile Gly Arg Gly Asp Ala Val Pro Ile Gly Asp Leu Val | |
|         230                 235                 240             | |

| ggc tgg ctg ctg gag gcc gcc gcc ttc ccg gag gac cgg gtc gac cgc | 1845 |
|---|---|
| Gly Trp Leu Leu Glu Ala Ala Ala Phe Pro Glu Asp Arg Val Asp Arg | |
| 245                 250                 255                     | |

| cgg gag gcg ccg gtg cgg agc aag ggc ggc gac tgg acc cgg ctg gac | 1893 |
|---|---|
| Arg Glu Ala Pro Val Arg Ser Lys Gly Gly Asp Trp Thr Arg Leu Asp | |
| 260                 265                 270                 275 | |

| atc ggg cgg gcc cgg cgg ttg ctg tcc tgg gcg ccg cgc atc ggc ctg | 1941 |
|---|---|
| Ile Gly Arg Ala Arg Arg Leu Leu Ser Trp Ala Pro Arg Ile Gly Leu | |

|  |  |  | 280 |  |  |  | 285 |  |  |  | 290 |  |  |  |
|---|---|---|---|---|---|---|---|---|---|---|---|---|---|---|
| cgg | gac | tcc | gtc | cac | agc | atg | tgg | cgg | acc | gcg | cac | ggc | gcc | ccg gcc | 1989 |
| Arg | Asp | Ser | Val | His | Ser | Met | Trp | Arg | Thr | Ala | His | Gly | Ala | Pro Ala |
|  |  |  | 295 |  |  |  | 300 |  |  |  | 305 |  |  |  |

```
tag ctcacaggct tccgacgacc tcccgcaccg cgtggatcac cttctcctgc      2042
gcgtcgggac gcagcgaggg gtacatcggc agggagaaga tctcgccggc cagccgttcg 2102
gtcaccggca ggtcgccggg gccgtagccg aggtgggcga atccgctcat ggtgtggacg 2162
ggccaggggt agctgatgtt gagatggatg tcgtaggcgg tgagcgcctc caggatgcgg 2222
tcgcgttcgg ggtgacgcac cacgtacacg tagtagacgt ggtcgttgcc ctcggcggtc 2282
gtgggcagca ccaggccgtc gaggtcaccg agtccctcct cgtagcggcg ggcgacggcc 2342
cggcggccct cgacataggc gtcgaggcgg cgcagtttcc ggcgcaggat ctcggcctgc 2402
acctcgtcga gcctgctgtt gtgcccgggg gtgtccacga cgtagtagcg ctcctccatg 2462
ccgtagtagc gcaaccgccg cagccgccgg tcgacttccg cgtccggcgt gacgacggcg 2522
ccgccgtcac cgtaggcacc gaggaccttg gtcgggtaga aggagaaggc cgccgcatgc 2582
ccctgggtgc cgaccagccg tccgtgacgg cgggcaccgt gggcctgggc gcagtcctcc 2642
agcaccttca ggtcgtgctc ggcggcgagt tcgagcacgg gggtcatgtc cacgctctgt 2702
ccgtagaggt ggacgggcag caggcaccgg gtgcgcgggc cgatcaccga ccggagccgg 2762
ccggtgtcca tgaggtagtt ctcctcgtgc acgtcgacga agacggggt ggcgcccacg 2822
gcgtcgatgg ccaccacggt gggggccgcg gtgttggaga ccgtcacgac ctcgtccccc 2882
gggccgatgc cgagcgcccg caggccgagg accagcgcgt tggtgccgtt gtcgacgccg 2942
gtgcagtacg gcagtccgtg ataagcggcg aactcctcct cgaaagagcg gacgctggtc 3002
ccgagaataa gctggccgga ctcgaatacc gtttccaccg catcgagaat gtcggtgcgt 3062
tcttcccggt attcattgag gtattgccag acgtaggtgg acacgtgact ccttgtcggg 3122
gcgcggtcag gcaagcgcga cggacgcggc tgccgggact tccggaccgt tccgtcgat  3182
gccggggtcg gccgcagaa tcgcgtgctg gaggtgctgg agacgggcgg acggttccac  3242
ccccagctcg ttcaccaatg tcttgcggag tttgatgaag gcttcgaggg cctggctcgt 3302
gcggcccgag cgatggaggg cgatcatgaa ttgggcccac aggttctcgt gcatggggtg 3362
acgggcggtg agcgccgaca gctcgggcag caggcccgcg tgccggccca gcctcaggtc 3422
ggtctccatg cgggcctcca ggacgccgag ccggctctcc tccaggcgcg ccacctccat 3482
gccgatccgc atgccggcgt gcacgtccac gagcgcgtct ccgcgccaca ggtcgagggc 3542
ctggcggaag cgtgcggagg ccaggtcgag ctcccccgc tcgcacgccc gcttgccctc  3602
ctcggcgaga cgctcgaagg cgtacacgtc ggtgtgggtg gggtccacgt cgagcaggta 3662
gccgccgtag caggtgcgca gcacgtcctt ggcgggtccg ttgtggctcg cgccgagggc 3722
cacggtgatg cccccggcgca cttgaaggat gtaggtctga aggtggtca gcgcgctcgc 3782
cgggggctgg gttccccaga gctcctccat cagcgcgggc accggcacga cggttcctgc 3842
ctggagagcg agcagtgaga atacttgccg ggttttctg gctatcgggg tcaccgacgt  3902
gccattgtga tgtgcgacga gcgggcccaa catattgatc tgcattgccg gtgtgctccc 3962
tctgtggcgt tccgatcgcg tcagcaggtg gcatatttcc ggcggccgaa ggatgtcctc 4022
gggcggcccc gtttgctcgc tccatcctcg caagtgaatg cccgccatga agtgtgtgc  4082
ggcacttgct gggattagtt catcacgtct cgatgtgaga aagtcacagt gggagcgccg 4142
gggagggatc cgcaccgggt acacggcacg ggaccgccca ccgcgcggtg cgcggtgggc 4202
```

```
ggtgggcggt cccgtgccgg tcgcggccgg cggatcagcg cagccagacg ggcagttcgg    4262
tgagccgcgc cgtctgggcc cccttccggg accaccgcaa ctcgtcgtac ggcacggcca    4322
gtcgcgcctc ggggaacctg ctgcgcagta cgccgatcat cgtgcgcgac tccagctggg    4382
cgagctgctc cccgatgcag tagtgcggcc cgtcgccgaa ggtgagccgc cgccacgagg    4442
gacggtccgg gtggaaggcg tgcgggtcgt cgtgatggcg gccgtcggtg ttggtgccct    4502
cgatgtccac cagcaccggc gctccgcggg gcagccggac ccgccgatg gtcacctccg    4562
tggcagcgaa cctccacaac gtgtagggca ccggcgggtg gtagcgcagc gcctcctcca    4622
cgaaccggga gaccgcgtcc tcgtcggcgt ccgccgcgag gcggcccgcc agcacctccg    4682
cgagcaggaa gcccaggaag gagccggtgg tgtcgtggcc ggcgaagatg agcccggtga    4742
tcatgtagac gagctggtcg tcggagaccg agccgaactc ggcctgcgcg cgttcgtaca    4802
gcacgcgggt catggtcggg gtgtcgttcc gccgggccga gtgcacggct tcgaggagca    4862
ggctctccag ggccgaggtg tccggcacgc ccccggcagg gtccgtgccg tcaccccgc    4922
cgctctgcgg gccgccgagg ccgagtgcct tgagaacgct gacggcctcg cgggccatcg    4982
ccggatcggt gaccggcacg ccgagcagct cgcagatgac caacagcggg aagtggtaag    5042
cgaaaccgcc gatcagctcg gccggttttgc ccgaccgccc ggaagtgtcg gcgagttcgg    5102
tgagcagccg gccggcgatg gcggcgatgc gatccgtccg ctcggccagc cggcgcgggt    5162
tgaacgcggg tgcgtggatg cggcgcaggc gccggtgggc ctcgccgtcc acggcgatga    5222
gcgtgaacgg acgcagctcc ggaacgggga tgtcgagacc gtcgtccacc ccccgccagg    5282
cggcggggc gaggtcgggg tccttcacga accggggatc ggccagcacc tcgcgggcga    5342
gggcgtcatc ggtgatgacc caggcgggtc cgcccgcggg ggcgttcacc tcgacgaccg    5402
ggcccgcctc ccggaaggcg tcgtgcacct cgggcttgcg ctgcatggtc atcatgggac    5462
acgcgaacgg gtcgacggcc acccggggcg cctcgccgct cacgaggcac cgcccgccgc    5522
cgcggggtac ccctcccgca gttcgaccac cgagaagccg gccccgtgcg ggtcgagcag    5582
gtccgcccgc cgccccctgg gcgtgtcggc gggctcgttc tcgacggagc cgccgagttc    5642
aacggcgcgc cggaccgtcg cgtcgcagtc gcgcacggcg aacagcacgg cccagtgcgg    5702
ccgtaccgcg ccggtgacgc ccagctcctg ggtgccggcg accggtgtgt caccgatgtg    5762
ccagaccggg tcggtgacgc ccttcaggcc ggtgtcggcc ggagccaggc cgagggtcgc    5822
cggatagaag tcccgggcgg ccccgatgcc gtcggtcacc agctcgaccc agccgaccga    5882
gccgggcacg cccgtcacct ccgcgccctc catgactccc ttgcgccaga ccgcgaacgc    5942
ggccccggcg gggtcggcga agaccgccat ccggccgagg ccgaggacgt ccatcggggt    6002
catgatgacc tcgccgcccg ccgtctcgac ccgcttggtc agtgcgtcgg cgtcgtcggt    6062
ggcgaagtac acggtccaga tggccggcat gccgtgctgg tcgttcccgg gcccgtacgg    6122
ccggtggtag ggggtgtcga tctggtggcg ggcgaccgcg cgaccagct tcccgtcgga    6182
gctgaacgtc gtgtatcccc cggcgcccgg gtcgctgacc acggtggcgg tccagccgaa    6242
caggccggta tagaagtcgg ccgaggcggc gacatcgggc gaaccgaggt cgaaccatgc    6302
gggggcgccg ggcgcgaacc tggtcacgaa tcgttccttt cgatggatcg gcacacgagc    6362
gtctgcgctc gcggatgaga cggacatctc gcggatgaga cggacatgcg gcggggcgg    6422
gccgccgccg tcagtgcgcg gtgtcgccga cggcggccgc gccggcctcc cagagcttcg    6482
ccgcgaggcc ggcgtcggcg gtcgggccgc tcaccgggga cagccgccgg tcgctgtagt    6542
agccgcccgt ggtcaactcc tcggccggcg cggacgccag ccacacgagg gtgtcggcgc    6602
```

-continued

```
ccttcgccgc ggagcgcagg aaggggttga accggaagta ggacgaggcg accgtgcccc    6662
gtccgatgcg ggtgcggacc tcgccggggt gatagctgac cgccagcacg tccggccagc    6722
gcctggcggc ctccgccgcg gtcatgatgt tggcctgttt ggacgtgccg tacgcctggc    6782
cggcgctgta gcggtgacgg tcgccgttga ggtcgtccgg gtcgatccgg ccctgggtgt    6842
acgcgtcgga cgaggtgagg atcagccgcc cgcccgcgag ccgctcccgc agcagccgtg    6902
ccagcaggaa acccgcgaga tgattgacct ggatggtggc ctcgaacccg tcctgggtcg    6962
tggtgcgcga ccagaacatg ccgccggcgt tgctggccat gacatcgatg cgcgggtacc    7022
ggtcccgcag ccgctccccc agatcgcgta cctggcgcag ctcggcgaag tccgcgcgga    7082
aggcgtccgg ggccgggccg gcggtccggg ccacctcgtt cgtgacggtc cgcagacgct    7142
cggggtcccg gccgacgagc acgacgcggg ccccctggcg ggcgaccgcg agggccgccg    7202
cccggccgat gccggacgtg gccccggtga ccagcaccgt ccggcccgac agggcgccgc    7262
gtggtgtccc gtggtacggg gtggggccgc tcatgccgcc gctacgcagc ctctcgttga    7322
cgaagatc                                                              7330
```

<210> SEQ ID NO 6
<211> LENGTH: 307
<212> TYPE: PRT
<213> ORGANISM: Streptomyces coeruleorubidus

<400> SEQUENCE: 6

```
Met Arg Val Val Leu Gly Ala Thr Gly Ser Val Gly Arg Gln Val
1               5                   10                  15

Cys Ala Ala Tyr Gln Ala His Gly Trp Asp Val His Gly Val Ala Arg
                20                  25                  30

Arg Pro Ala Pro His Leu Ser Gly Cys Gly Phe Thr Glu Leu Asp Leu
            35                  40                  45

Ala Ala Ala Ala Pro Gly Arg Ile Ala Thr Val Leu Gly Asp Pro Pro
        50                  55                  60

Ala Asp Val Val Asn Ala Ala Gly Gly Trp Gly Asp Thr Glu Glu
65                  70                  75                  80

Glu Met Thr Tyr Ser His Leu Arg Leu Val Arg Arg Leu Val Glu Ala
                85                  90                  95

Leu Ala Leu Leu Pro Phe Arg Pro Arg Leu Val His Leu Gly Ser Val
            100                 105                 110

His Glu Tyr Gly Pro Val Pro Ala Gly Thr Leu Leu His Glu Asp Leu
        115                 120                 125

Pro Pro Glu Pro Val Thr Pro Tyr Ala Arg Val Lys Leu Glu Thr Ser
    130                 135                 140

Ser Ala Val Leu Thr Ala Ala Arg Ala Gly Val Leu Asp Ala Val Val
145                 150                 155                 160

Leu Arg Ala Ala Asn Met Ser Gly Pro His Pro Pro Gln Glu Ser Phe
                165                 170                 175

Leu Ala Ala Leu Met Ala Arg Ile Ser Thr Ala Phe Ala His Gly Gly
            180                 185                 190

Arg Leu Glu Leu Ser Val Ala Asp Ala Arg Arg Asp Phe Val Asp Val
        195                 200                 205

Arg Asp Val Ala Gln Ala Val Arg Ala Gly Arg Ala Pro Ala Val
    210                 215                 220

Gly Gly Leu Val Val Asn Ile Gly Arg Gly Asp Ala Val Pro Ile Gly
225                 230                 235                 240

Asp Leu Val Gly Trp Leu Leu Glu Ala Ala Ala Phe Pro Glu Asp Arg
```

```
                245                 250                 255
Val Asp Arg Arg Glu Ala Pro Val Arg Ser Lys Gly Gly Asp Trp Thr
            260                 265                 270

Arg Leu Asp Ile Gly Arg Ala Arg Arg Leu Leu Ser Trp Ala Pro Arg
        275                 280                 285

Ile Gly Leu Arg Asp Ser Val His Ser Met Trp Arg Thr Ala His Gly
    290                 295                 300

Ala Pro Ala
305

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
gggaagcttg atcgccctca cggaactgcg caggcgcgg                              39

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
cgcagatgcg actacgtcat ctcc                                              24

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
gggtctagag ccggcatgcg gatcggcatg gaggtg                                 36

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10
atgctgggca tctacgtc                                                     18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
accgtactcg tgcaccga                                                     18
```

```
<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
gggtgatcaa gcgaaggaga agtatgaggc tcactaccg                         39

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
gggtctagat caagaactca ccgccgg                                      27

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14
gggggatcca gcgaaggagc aaagctccga tgaatggga                         39

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
gggtctagac tagtgctcct cggtggg                                      27

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16
gggggatcca gcgaaggagg ggccaccaga tgggg                             35

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 17
gggtctagac tacacgtaag ccgccac                                      27

<210> SEQ ID NO 18
<211> LENGTH: 39
```

-continued

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
gggggatcca gcgaaggagg cagcggcccc atgagatgg                             39

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
gggtctagat catgctgctc ctcgccgg                                        28

<210> SEQ ID NO 20
<211> LENGTH: 1049
<212> TYPE: DNA
<213> ORGANISM: Streptomyces mycarofaciens
<220> FEATURE:
<221> NAME/KEY: CDS
<222> LOCATION: (21)..(1043)

<400> SEQUENCE: 20

```
agatctagcg aaggagaagt atg agg ctc act acc gag ttg ttc aag cgg tcg      53
                     Met Arg Leu Thr Thr Glu Leu Phe Lys Arg Ser
                      1               5                  10 cac cat ccg cgc ggg cca ttg gtc acg gtg ctc ggc gcg tcg gga ttc       101
His His Pro Arg Gly Pro Leu Val Thr Val Leu Gly Ala Ser Gly Phe
             15                  20                  25 ctc ggg tcc gcc gtg gtg gcc gaa ctc gcc gca ctg ccg ctg cgc ttg       149
Leu Gly Ser Ala Val Val Ala Glu Leu Ala Ala Leu Pro Leu Arg Leu
         30                  35                  40 cgc ctg gtg gcg cgc ggt ccc agc cgt gtg ccg gcc gaa ccg gtg gcg       197
Arg Leu Val Ala Arg Gly Pro Ser Arg Val Pro Ala Glu Pro Val Ala
     45                  50                  55 gac atc gag gtg cgc cgg acg gac ctc gcc cgg ccg gac gcc gtc gcg       245
Asp Ile Glu Val Arg Arg Thr Asp Leu Ala Arg Pro Asp Ala Val Ala
 60                  65                  70                  75 gcc gcc gcc gag ggc gcg gac gcc gtc gtt cat ctc gcg gcg ggg atc       293
Ala Ala Ala Glu Gly Ala Asp Ala Val Val His Leu Ala Ala Gly Ile
                 80                  85                  90 ggc gga cag cag tcc tgg cgc gcc gcc gac gag cac gcg gag cgg gtg       341
Gly Gly Gln Gln Ser Trp Arg Ala Ala Asp Glu His Ala Glu Arg Val
             95                 100                 105 aac gtc ggc atg atg cgc gac ctt gtc gat gcg ctg cgc ggc cgg agc       389
Asn Val Gly Met Met Arg Asp Leu Val Asp Ala Leu Arg Gly Arg Ser
         110                 115                 120 ggc gcc cgg ccg gcc gtg gcc ttc gcc agc acg ctc cag gcc ggg tcc       437
Gly Ala Arg Pro Ala Val Ala Phe Ala Ser Thr Leu Gln Ala Gly Ser
     125                 130                 135 ccc acg ggc aac gcc gcc ccc ctg ggc ggc tac gca tcg cag aag atc       485
Pro Thr Gly Asn Ala Ala Pro Leu Gly Gly Tyr Ala Ser Gln Lys Ile
140                 145                 150                 155 gcc gcc gag ggg atc ctg cgc gag gcc acg gcc gag ggc gtc gtc cgc       533
Ala Ala Glu Gly Ile Leu Arg Glu Ala Thr Ala Glu Gly Val Val Arg
                 160                 165                 170 ggc gtc gtg ctg cgg ctg tcg acc ctg tac ggc cac agc ccg ctc tcc       581
Gly Val Val Leu Arg Leu Ser Thr Leu Tyr Gly His Ser Pro Leu Ser
```

```
                       175                 180                 185
ggc ggc gcc ggg cgc ggc gtg ctc gcg tcg atg acc cgc cgc gcc ctc       629
Gly Gly Ala Gly Arg Gly Val Leu Ala Ser Met Thr Arg Arg Ala Leu
        190                 195                 200 gac ggc gaa gcc ctg acc atg tgg cat gac gga tcg gtc ggg cgc gac       677
Asp Gly Glu Ala Leu Thr Met Trp His Asp Gly Ser Val Gly Arg Asp
205                 210                 215 ttc ctc cac gtc cgg gac gct gcg ggc gcc ttc acg gct gcc ctg gag       725
Phe Leu His Val Arg Asp Ala Ala Gly Ala Phe Thr Ala Ala Leu Glu
220                 225                 230                 235 cat gcg gcg gag cta cag ggc gag ccc tgg atc gtc gca acc ggc cgc       773
His Ala Ala Glu Leu Gln Gly Glu Pro Trp Ile Val Ala Thr Gly Arg
            240                 245                 250 ctg gag cgg ctc ggt gac gtg ttc acc gcc ctg gct ggt ctc gtg gcc       821
Leu Glu Arg Leu Gly Asp Val Phe Thr Ala Leu Ala Gly Leu Val Ala
                255                 260                 265 gag cac acc ggc ggg act ccg gct ccg gtc gtc gcc gtg cca ccc ccc       869
Glu His Thr Gly Gly Thr Pro Ala Pro Val Val Ala Val Pro Pro Pro
                    270                 275                 280 gct tac gcc gaa gcg ggt gat ttc cac agc ccg gag tcc gac tcc gcc       917
Ala Tyr Ala Glu Ala Gly Asp Phe His Ser Pro Glu Ser Asp Ser Ala
285                 290                 295 gcc ttc cgg gct gtg acc ggc tgg gct ccc cgg gtg cgg ttc ccc gag       965
Ala Phe Arg Ala Val Thr Gly Trp Ala Pro Arg Val Arg Phe Pro Glu
300                 305                 310                 315 ggg ctg cgg gac atg gtc gcg gcg atc gcc gcc gtg cac ccc gca ccg      1013
Gly Leu Arg Asp Met Val Ala Ala Ile Ala Ala Val His Pro Ala Pro
            320                 325                 330 ccg gct gcg cac ccg gcg gtg agt tct tga tctaga                       1049
Pro Ala Ala His Pro Ala Val Ser Ser
            335                 340

<210> SEQ ID NO 21
<211> LENGTH: 340
<212> TYPE: PRT
<213> ORGANISM: Streptomyces mycarofaciens

<400> SEQUENCE: 21

Met Arg Leu Thr Thr Glu Leu Phe Lys Arg Ser His His Pro Arg Gly
1               5                   10                  15

Pro Leu Val Thr Val Leu Gly Ala Ser Gly Phe Leu Gly Ser Ala Val
                20                  25                  30

Val Ala Glu Leu Ala Ala Leu Pro Leu Arg Leu Arg Leu Val Ala Arg
            35                  40                  45

Gly Pro Ser Arg Val Pro Ala Glu Pro Val Ala Asp Ile Glu Val Arg
        50                  55                  60

Arg Thr Asp Leu Ala Arg Pro Asp Ala Val Ala Ala Ala Glu Gly
65                  70                  75                  80

Ala Asp Ala Val Val His Leu Ala Ala Gly Ile Gly Gly Gln Gln Ser
                85                  90                  95

Trp Arg Ala Ala Asp Glu His Ala Glu Arg Val Asn Val Gly Met Met
            100                 105                 110

Arg Asp Leu Val Asp Ala Leu Arg Gly Arg Ser Gly Ala Arg Pro Ala
        115                 120                 125

Val Ala Phe Ala Ser Thr Leu Gln Ala Gly Ser Pro Thr Gly Asn Ala
    130                 135                 140

Ala Pro Leu Gly Gly Tyr Ala Ser Gln Lys Ile Ala Ala Glu Gly Ile
145                 150                 155                 160
```

```
Leu Arg Glu Ala Thr Ala Glu Gly Val Val Arg Gly Val Val Leu Arg
                165                 170                 175

Leu Ser Thr Leu Tyr Gly His Ser Pro Leu Ser Gly Gly Ala Gly Arg
            180                 185                 190

Gly Val Leu Ala Ser Met Thr Arg Arg Ala Leu Asp Gly Glu Ala Leu
        195                 200                 205

Thr Met Trp His Asp Gly Ser Val Gly Arg Asp Phe Leu His Val Arg
    210                 215                 220

Asp Ala Ala Gly Ala Phe Thr Ala Ala Leu Glu His Ala Ala Glu Leu
225                 230                 235                 240

Gln Gly Glu Pro Trp Ile Val Ala Thr Gly Arg Leu Glu Arg Leu Gly
                245                 250                 255

Asp Val Phe Thr Ala Leu Ala Gly Leu Val Ala Glu His Thr Gly Gly
            260                 265                 270

Thr Pro Ala Pro Val Val Ala Val Pro Pro Ala Tyr Ala Glu Ala
        275                 280                 285

Gly Asp Phe His Ser Pro Glu Ser Asp Ser Ala Ala Phe Arg Ala Val
    290                 295                 300

Thr Gly Trp Ala Pro Arg Val Arg Phe Pro Glu Gly Leu Arg Asp Met
305                 310                 315                 320

Val Ala Ala Ile Ala Ala Val His Pro Ala Pro Pro Ala Ala His Pro
                325                 330                 335

Ala Val Ser Ser
            340

<210> SEQ ID NO 22
<211> LENGTH: 1001
<212> TYPE: DNA
<213> ORGANISM: Saccharopolyspora erythraea
<220> FEATURE:
<221> NAME/KEY: CDS
<222> LOCATION: (27)..(995)

<400> SEQUENCE: 22
ggatccagcg aaggagcaaa gctccg atg aat ggg atc agt gat tcc ccg cgt      53
                              Met Asn Gly Ile Ser Asp Ser Pro Arg
                                1               5 caa ttg atc acc ctt ctg ggc gct tcc ggc ttc gtc ggg agc gcg gtt     101
Gln Leu Ile Thr Leu Leu Gly Ala Ser Gly Phe Val Gly Ser Ala Val
 10              15                  20                  25 ctg cgc gag ctg cgc gac cac ccg gtc cgg ctg cgc gcg gtg tcc cgc     149
Leu Arg Glu Leu Arg Asp His Pro Val Arg Leu Arg Ala Val Ser Arg
             30                  35                  40 ggc gga gcg ccc gcg gtt ccg ccc ggc gcc gcg gag gtc gag gac ctg     197
Gly Gly Ala Pro Ala Val Pro Pro Gly Ala Ala Glu Val Glu Asp Leu
         45                  50                  55 cgc gcc gac ctg ctg gaa ccg ggc cgg gcc gcc gcc gcg atc gag gac     245
Arg Ala Asp Leu Leu Glu Pro Gly Arg Ala Ala Ala Ala Ile Glu Asp
     60                  65                  70 gcc gac gtg atc gtg cac ctg gtg gcg cac gca gcg ggc ggt tcc acc     293
Ala Asp Val Ile Val His Leu Val Ala His Ala Ala Gly Gly Ser Thr
 75                  80                  85 tgg cgc agc gcc acc tcc gac ccg gaa gcc gag cgg gtc aac gtc ggc     341
Trp Arg Ser Ala Thr Ser Asp Pro Glu Ala Glu Arg Val Asn Val Gly
 90                  95                 100                 105 ctg atg cac gac ctc gtc ggc gcg ctg cac gat cgc cgc agg tcg acg     389
Leu Met His Asp Leu Val Gly Ala Leu His Asp Arg Arg Arg Ser Thr
            110                 115                 120 ccg ccc gtg ttg ctc tac gcg agc acc gca cag gcc gcg aac ccg tcg     437
```

```
Pro Pro Val Leu Leu Tyr Ala Ser Thr Ala Gln Ala Ala Asn Pro Ser
            125                 130                 135 gcg gcc agc agg tac gcg cag cag aag acc gag gcc gag cgc atc ctg       485
Ala Ala Ser Arg Tyr Ala Gln Gln Lys Thr Glu Ala Glu Arg Ile Leu
        140                 145                 150 cgc aaa gcc acc gac gag ggc cgg gtg cgc ggc gtg atc ctg cgg ctg       533
Arg Lys Ala Thr Asp Glu Gly Arg Val Arg Gly Val Ile Leu Arg Leu
    155                 160                 165 ccc gcc gtc tac ggc cag agc ggc ccg tcc ggc ccc atg ggg cgg ggc       581
Pro Ala Val Tyr Gly Gln Ser Gly Pro Ser Gly Pro Met Gly Arg Gly
170                 175                 180                 185 gtg gtc gca gcg atg atc cgg cgt gcc ctc gcc ggc gag ccg ctc acc       629
Val Val Ala Ala Met Ile Arg Arg Ala Leu Ala Gly Glu Pro Leu Thr
                190                 195                 200 atg tgg cac gac ggc ggc gtg cgc cgc gac ctg ctg cac gtc gag gac       677
Met Trp His Asp Gly Gly Val Arg Arg Asp Leu Leu His Val Glu Asp
            205                 210                 215 gtg gcc acc gcg ttc gcc gcc gcg ctg gag cac cac gac gcg ctg gcc       725
Val Ala Thr Ala Phe Ala Ala Ala Leu Glu His His Asp Ala Leu Ala
        220                 225                 230 ggc ggc acg tgg gcg ctg ggc gcc gac cga tcc gag ccg ctc ggc gac       773
Gly Gly Thr Trp Ala Leu Gly Ala Asp Arg Ser Glu Pro Leu Gly Asp
    235                 240                 245 atc ttc cgg gcc gtc tcc ggc agc gtc gcc cgg cag acc ggc agc ccc       821
Ile Phe Arg Ala Val Ser Gly Ser Val Ala Arg Gln Thr Gly Ser Pro
250                 255                 260                 265 gcc gtc gac gtg gtc acc gtg ccc gcg ccc gag cac gcc gag gcc aac       869
Ala Val Asp Val Val Thr Val Pro Ala Pro Glu His Ala Glu Ala Asn
                270                 275                 280 gac ttc cgc agc gac gac atc gac tcc acc gag ttc cgc agc cgg acc       917
Asp Phe Arg Ser Asp Asp Ile Asp Ser Thr Glu Phe Arg Ser Arg Thr
            285                 290                 295 ggc tgg cgc ccc cgg gtt tcc ctc acc gac ggc atc gac cgg acg gtg       965
Gly Trp Arg Pro Arg Val Ser Leu Thr Asp Gly Ile Asp Arg Thr Val
        300                 305                 310 gcc gcc ctg acc ccc acc gag gag cac tag tctaga                       1001
Ala Ala Leu Thr Pro Thr Glu Glu His
    315                 320

<210> SEQ ID NO 23
<211> LENGTH: 322
<212> TYPE: PRT
<213> ORGANISM: Saccharopolyspora erythraea

<400> SEQUENCE: 23

Met Asn Gly Ile Ser Asp Ser Pro Arg Gln Leu Ile Thr Leu Leu Gly
1               5                   10                  15

Ala Ser Gly Phe Val Gly Ser Ala Val Leu Arg Glu Leu Arg Asp His
            20                  25                  30

Pro Val Arg Leu Arg Ala Val Ser Arg Gly Gly Ala Pro Ala Val Pro
        35                  40                  45

Pro Gly Ala Ala Glu Val Glu Asp Leu Arg Ala Asp Leu Leu Glu Pro
    50                  55                  60

Gly Arg Ala Ala Ala Ile Glu Asp Ala Asp Val Ile Val His Leu
65                  70                  75                  80

Val Ala His Ala Ala Gly Gly Ser Thr Trp Arg Ser Ala Thr Ser Asp
                85                  90                  95

Pro Glu Ala Glu Arg Val Asn Val Gly Leu Met His Asp Leu Val Gly
            100                 105                 110
```

```
Ala Leu His Asp Arg Arg Arg Ser Thr Pro Pro Val Leu Leu Tyr Ala
        115                 120                 125

Ser Thr Ala Gln Ala Ala Asn Pro Ser Ala Ala Ser Arg Tyr Ala Gln
130                 135                 140

Gln Lys Thr Glu Ala Glu Arg Ile Leu Arg Lys Ala Thr Asp Glu Gly
145                 150                 155                 160

Arg Val Arg Gly Val Ile Leu Arg Leu Pro Ala Val Tyr Gly Gln Ser
                165                 170                 175

Gly Pro Ser Gly Pro Met Gly Arg Gly Val Ala Ala Met Ile Arg
            180                 185                 190

Arg Ala Leu Ala Gly Glu Pro Leu Thr Met Trp His Asp Gly Val
        195                 200                 205

Arg Arg Asp Leu Leu His Val Glu Asp Val Ala Thr Ala Phe Ala Ala
        210                 215                 220

Ala Leu Glu His His Asp Ala Leu Ala Gly Gly Thr Trp Ala Leu Gly
225                 230                 235                 240

Ala Asp Arg Ser Glu Pro Leu Gly Asp Ile Phe Arg Ala Val Ser Gly
                245                 250                 255

Ser Val Ala Arg Gln Thr Gly Ser Pro Ala Val Asp Val Thr Val
            260                 265                 270

Pro Ala Pro Glu His Ala Glu Ala Asn Asp Phe Arg Ser Asp Asp Ile
        275                 280                 285

Asp Ser Thr Glu Phe Arg Ser Arg Thr Gly Trp Arg Pro Arg Val Ser
290                 295                 300

Leu Thr Asp Gly Ile Asp Arg Thr Val Ala Ala Leu Thr Pro Thr Glu
305                 310                 315                 320

Glu His

<210> SEQ ID NO 24
<211> LENGTH: 1064
<212> TYPE: DNA
<213> ORGANISM: Streptomyces avermitilis
<220> FEATURE:
<221> NAME/KEY: CDS
<222> LOCATION: (27)..(1058)

<400> SEQUENCE: 24
ggatccagcg aaggagggc caccag atg ggg cgg ttt tcg gtg tgc ccg ccc      53
                             Met Gly Arg Phe Ser Val Cys Pro Pro
                              1               5 cgg ccg acc gga ata ctg aag agc atg ctg acg act ggg atg tgc gac    101
Arg Pro Thr Gly Ile Leu Lys Ser Met Leu Thr Thr Gly Met Cys Asp
 10                  15                  20                  25 cga ccg ctg gtc gtc gta ctc gga gcc tcc ggc tat atc ggg tcg gcc    149
Arg Pro Leu Val Val Val Leu Gly Ala Ser Gly Tyr Ile Gly Ser Ala
                 30                  35                  40 gtc gcg gcg gaa ctc gcc cgg tgg ccg gtc ctg ttg cgg ctg gtg gcc    197
Val Ala Ala Glu Leu Ala Arg Trp Pro Val Leu Leu Arg Leu Val Ala
             45                  50                  55 cgg cga ccg ggc gtc gtt ccg ccg ggc ggc gcc gcg gag acc gag acg    245
Arg Arg Pro Gly Val Val Pro Pro Gly Gly Ala Ala Glu Thr Glu Thr
         60                  65                  70 cgt acg gcc gac ctg acg gcg gcg agc gag gtc gcc ctc gcc gtg acg    293
Arg Thr Ala Asp Leu Thr Ala Ala Ser Glu Val Ala Leu Ala Val Thr
     75                  80                  85 gac gcc gac gtg gtg atc cac ctg gtc gcg cgc ctc acc cag gga gcg    341
Asp Ala Asp Val Val Ile His Leu Val Ala Arg Leu Thr Gln Gly Ala
 90                  95                 100                 105
```

| | | | | | | | | | | | | | | | | |
|---|---|---|---|---|---|---|---|---|---|---|---|---|---|---|---|---|
| gca | tgg | cgg | gcg | gcg | gag | agc | gat | ccg | gtg | gcc | gag | cgg | gtg | aac | gtc | 389 |
| Ala | Trp | Arg | Ala | Ala | Glu | Ser | Asp | Pro | Val | Ala | Glu | Arg | Val | Asn | Val | |
| | | | 110 | | | | | 115 | | | | | 120 | | | |
| ggg | gtg | atg | cac | gac | gtc | gtc | gcg | gcc | ctg | cgg | tcc | ggg | cgc | cgc | gcc | 437 |
| Gly | Val | Met | His | Asp | Val | Val | Ala | Ala | Leu | Arg | Ser | Gly | Arg | Arg | Ala | |
| | | 125 | | | | | 130 | | | | | 135 | | | | |
| ggg | ccg | ccc | ccg | gtg | gtg | gtg | ttc | gcc | ggg | tcg | gtc | tac | cag | gtg | ggc | 485 |
| Gly | Pro | Pro | Pro | Val | Val | Val | Phe | Ala | Gly | Ser | Val | Tyr | Gln | Val | Gly | |
| | | 140 | | | | | 145 | | | | | 150 | | | | |
| cgc | ccg | ggt | cgg | gtc | gac | ggc | agt | gag | ccg | gac | gag | ccc | gtg | acg | gcc | 533 |
| Arg | Pro | Gly | Arg | Val | Asp | Gly | Ser | Glu | Pro | Asp | Glu | Pro | Val | Thr | Ala | |
| | 155 | | | | | 160 | | | | | 165 | | | | | |
| tat | gcc | cgt | cag | aaa | ctc | gac | gcc | gaa | cgg | acg | ttg | aag | tcc | gcc | acg | 581 |
| Tyr | Ala | Arg | Gln | Lys | Leu | Asp | Ala | Glu | Arg | Thr | Leu | Lys | Ser | Ala | Thr | |
| 170 | | | | | 175 | | | | | 180 | | | | | 185 | |
| gtc | gag | ggt | gtc | ctg | cgg | ggg | atc | tcg | ctg | cgg | ctg | ccc | acc | gtc | tac | 629 |
| Val | Glu | Gly | Val | Leu | Arg | Gly | Ile | Ser | Leu | Arg | Leu | Pro | Thr | Val | Tyr | |
| | | | 190 | | | | | 195 | | | | | 200 | | | |
| ggc | gcg | ggg | ccg | ggc | ccg | cag | ggc | aac | ggc | gtc | gtg | cag | gcg | atg | gtg | 677 |
| Gly | Ala | Gly | Pro | Gly | Pro | Gln | Gly | Asn | Gly | Val | Val | Gln | Ala | Met | Val | |
| | | 205 | | | | | 210 | | | | | 215 | | | | |
| ctc | cgg | gcg | ctc | gcc | gac | gag | gcc | ctc | acc | gtg | tgg | aac | gga | agc | gtg | 725 |
| Leu | Arg | Ala | Leu | Ala | Asp | Glu | Ala | Leu | Thr | Val | Trp | Asn | Gly | Ser | Val | |
| | 220 | | | | | 225 | | | | | 230 | | | | | |
| gtg | gag | cgt | gac | ctg | gtg | cat | gtg | gag | gat | gtc | gcg | cag | gcc | ttc | gtg | 773 |
| Val | Glu | Arg | Asp | Leu | Val | His | Val | Glu | Asp | Val | Ala | Gln | Ala | Phe | Val | |
| | 235 | | | | | 240 | | | | | 245 | | | | | |
| agc | tgc | ctg | gcg | cac | gcg | gat | gcg | ctc | gcc | ggg | cgg | cac | tgg | ctg | ctc | 821 |
| Ser | Cys | Leu | Ala | His | Ala | Asp | Ala | Leu | Ala | Gly | Arg | His | Trp | Leu | Leu | |
| 250 | | | | | 255 | | | | | 260 | | | | | 265 | |
| ggc | agc | ggt | cgt | cct | gtg | acc | gtc | ccg | cac | ctc | ttc | ggt | gcc | atc | gcc | 869 |
| Gly | Ser | Gly | Arg | Pro | Val | Thr | Val | Pro | His | Leu | Phe | Gly | Ala | Ile | Ala | |
| | | | 270 | | | | | 275 | | | | | 280 | | | |
| gcc | ggc | gtg | tcc | gcc | cgc | acc | ggg | cgc | ccc | gcg | gtg | ccc | gtg | acc | gcg | 917 |
| Ala | Gly | Val | Ser | Ala | Arg | Thr | Gly | Arg | Pro | Ala | Val | Pro | Val | Thr | Ala | |
| | | 285 | | | | | 290 | | | | | 295 | | | | |
| gtg | gac | cct | ccg | gcg | atg | gcg | acg | gcg | gcg | gac | ttc | cac | ggg | acc | gtc | 965 |
| Val | Asp | Pro | Pro | Ala | Met | Ala | Thr | Ala | Ala | Asp | Phe | His | Gly | Thr | Val | |
| | | 300 | | | | | 305 | | | | | 310 | | | | |
| gtc | gac | tcc | tcg | gcg | ttc | cgc | gcg | gtc | acc | ggg | tgg | cgg | ccg | cgg | ctg | 1013 |
| Val | Asp | Ser | Ser | Ala | Phe | Arg | Ala | Val | Thr | Gly | Trp | Arg | Pro | Arg | Leu | |
| | | 315 | | | | | 320 | | | | | 325 | | | | |
| tcg | ctt | cag | gag | ggc | ctg | gac | cac | atg | gtg | gcg | gct | tac | gtg | tag | | 1058 |
| Ser | Leu | Gln | Glu | Gly | Leu | Asp | His | Met | Val | Ala | Ala | Tyr | Val | | | |
| 330 | | | | | 335 | | | | | 340 | | | | | | |
| tctaga | | | | | | | | | | | | | | | | 1064 |

<210> SEQ ID NO 25
<211> LENGTH: 343
<212> TYPE: PRT
<213> ORGANISM: Streptomyces avermitilis

<400> SEQUENCE: 25

Met Gly Arg Phe Ser Val Cys Pro Pro Arg Pro Thr Gly Ile Leu Lys
1               5                   10                  15

Ser Met Leu Thr Thr Gly Met Cys Asp Arg Pro Leu Val Val Leu
            20                  25                  30

Gly Ala Ser Gly Tyr Ile Gly Ser Ala Val Ala Ala Glu Leu Ala Arg
            35                  40                  45

Trp Pro Val Leu Leu Arg Leu Val Ala Arg Arg Pro Gly Val Val Pro

```
                50                  55                  60
Pro Gly Gly Ala Ala Glu Thr Glu Thr Arg Thr Ala Asp Leu Thr Ala
 65                  70                  75                  80

Ala Ser Glu Val Ala Leu Ala Val Thr Asp Ala Asp Val Val Ile His
                 85                  90                  95

Leu Val Ala Arg Leu Thr Gln Gly Ala Ala Trp Arg Ala Ala Glu Ser
            100                 105                 110

Asp Pro Val Ala Glu Arg Val Asn Val Gly Val Met His Asp Val Val
        115                 120                 125

Ala Ala Leu Arg Ser Gly Arg Arg Ala Gly Pro Pro Val Val Val
130                 135                 140

Phe Ala Gly Ser Val Tyr Gln Val Gly Arg Pro Gly Arg Val Asp Gly
145                 150                 155                 160

Ser Glu Pro Asp Glu Pro Val Thr Ala Tyr Ala Arg Gln Lys Leu Asp
                165                 170                 175

Ala Glu Arg Thr Leu Lys Ser Ala Thr Val Glu Gly Val Leu Arg Gly
            180                 185                 190

Ile Ser Leu Arg Leu Pro Thr Val Tyr Gly Ala Gly Pro Gly Pro Gln
        195                 200                 205

Gly Asn Gly Val Val Gln Ala Met Val Leu Arg Ala Leu Ala Asp Glu
210                 215                 220

Ala Leu Thr Val Trp Asn Gly Ser Val Val Glu Arg Asp Leu Val His
225                 230                 235                 240

Val Glu Asp Val Ala Gln Ala Phe Val Ser Cys Leu Ala His Ala Asp
                245                 250                 255

Ala Leu Ala Gly Arg His Trp Leu Leu Gly Ser Gly Arg Pro Val Thr
            260                 265                 270

Val Pro His Leu Phe Gly Ala Ile Ala Ala Gly Val Ser Ala Arg Thr
        275                 280                 285

Gly Arg Pro Ala Val Pro Val Thr Ala Val Asp Pro Pro Ala Met Ala
290                 295                 300

Thr Ala Ala Asp Phe His Gly Thr Val Val Asp Ser Ser Ala Phe Arg
305                 310                 315                 320

Ala Val Thr Gly Trp Arg Pro Arg Leu Ser Leu Gln Glu Gly Leu Asp
                325                 330                 335

His Met Val Ala Ala Tyr Val
            340

<210> SEQ ID NO 26
<211> LENGTH: 918
<212> TYPE: DNA
<213> ORGANISM: Streptomyces olivochromogenes
<220> FEATURE:
<221> NAME/KEY: CDS
<222> LOCATION: (28)..(912)

<400> SEQUENCE: 26
ggatccagcg aaggaggcag cggcccc atg aga tgg ctg atc acc ggc gcc gcc        54
                            Met Arg Trp Leu Ile Thr Gly Ala Ala
                             1               5 gga atg ctg ggc cgg gaa ctc gtc cgg cgc ctc gcc gag aac gag gag         102
Gly Met Leu Gly Arg Glu Leu Val Arg Arg Leu Ala Glu Asn Glu Glu
 10                  15                  20                  25 gac gtc gcg gct ctc ggc cac gac cac ctc gac gtc acc cgt ccc tcc         150
Asp Val Ala Ala Leu Gly His Asp His Leu Asp Val Thr Arg Pro Ser
                 30                  35                  40 gcc gtg cgg gcg gca ctc gcc gag cac cgt ccc ggg atc gtc gtc aac         198
```

```
                                                                                  -continued Ala Val Arg Ala Ala Leu Ala Glu His Arg Pro Gly Ile Val Val Asn
            45                  50                  55 tgc gcc gcc tac acg gcc gtc gac gac gcc gag acg gac gag gcc gcc        246
Cys Ala Ala Tyr Thr Ala Val Asp Asp Ala Glu Thr Asp Glu Ala Ala
         60                  65                  70 gct gcc ctc ctc aac gcc gag gcg ccc cgg ctg ctg gcc gag gcc tgc        294
Ala Ala Leu Leu Asn Ala Glu Ala Pro Arg Leu Leu Ala Glu Ala Cys
 75                  80                  85 gcc ccc cac ggc gca cgc ctc gtc cac ctg tcc acc gac tac gtc ttt        342
Ala Pro His Gly Ala Arg Leu Val His Leu Ser Thr Asp Tyr Val Phe
 90                  95                 100                 105 ccc ggc gac gcc cgc acc ccc tac gcc gag gac cac ccc acg gct ccc        390
Pro Gly Asp Ala Arg Thr Pro Tyr Ala Glu Asp His Pro Thr Ala Pro
             110                 115                 120 cgc agc gcc tac gga cgc acc aaa cgg gac ggc gag caa gcg gtg ctg        438
Arg Ser Ala Tyr Gly Arg Thr Lys Arg Asp Gly Glu Gln Ala Val Leu
         125                 130                 135 acg gca ctg ccc acc gcc acc gtg ctg cgc acc gcc tgg ctg tac ggg        486
Thr Ala Leu Pro Thr Ala Thr Val Leu Arg Thr Ala Trp Leu Tyr Gly
     140                 145                 150 cgc acc ggc cgc agc ttc gtc cgc acg atg atc gaa cgg gag gcg cgc        534
Arg Thr Gly Arg Ser Phe Val Arg Thr Met Ile Glu Arg Glu Ala Arg
 155                 160                 165 ggc ggc gcc atc gac gtc gtc gcc gac cag cgc ggc cag ccc acc tgg        582
Gly Gly Ala Ile Asp Val Val Ala Asp Gln Arg Gly Gln Pro Thr Trp
170                 175                 180                 185 acc ggc gac ctc gcc gac cgc atc gtc gcc gtc ggc cgg ctc ccc ggc        630
Thr Gly Asp Leu Ala Asp Arg Ile Val Ala Val Gly Arg Leu Pro Gly
             190                 195                 200 gtc cac ggc atc ctg cac gcc acc aac gcc ggc tcc gcc acc tgg tac        678
Val His Gly Ile Leu His Ala Thr Asn Ala Gly Ser Ala Thr Trp Tyr
         205                 210                 215 gac ctc gca caa gag gtc ttc cgg ctc ctc ggc gcc gac ccc ggg cgg        726
Asp Leu Ala Gln Glu Val Phe Arg Leu Leu Gly Ala Asp Pro Gly Arg
     220                 225                 230 gtc cgg ccc acc acc ggc gcc gcc ttc cgc aga ccc gct ccc cgc ccc        774
Val Arg Pro Thr Thr Gly Ala Ala Phe Arg Arg Pro Ala Pro Arg Pro
 235                 240                 245 gcc tac agc gtc ctc ggc cac gac cgc tgg cgc ggg acc ggc ctc gta        822
Ala Tyr Ser Val Leu Gly His Asp Arg Trp Arg Gly Thr Gly Leu Val
250                 255                 260                 265 ccc ctg cgt gac tgg cgc tcg gcc ctg cgc gag gcg ttc ccc gac atc        870
Pro Leu Arg Asp Trp Arg Ser Ala Leu Arg Glu Ala Phe Pro Asp Ile
             270                 275                 280 ctc gcc gcg gaa cac cca ccg acc cgg cga gga gca gca tga tctaga       918
Leu Ala Ala Glu His Pro Pro Thr Arg Arg Gly Ala Ala
         285                 290

<210> SEQ ID NO 27
<211> LENGTH: 294
<212> TYPE: PRT
<213> ORGANISM: Streptomyces olivochromogenes

<400> SEQUENCE: 27

Met Arg Trp Leu Ile Thr Gly Ala Ala Gly Met Leu Gly Arg Glu Leu
1               5                   10                  15

Val Arg Arg Leu Ala Glu Asn Glu Glu Asp Val Ala Ala Leu Gly His
            20                  25                  30

Asp His Leu Asp Val Thr Arg Pro Ser Ala Val Arg Ala Ala Leu Ala
        35                  40                  45
```

```
Glu His Arg Pro Gly Ile Val Val Asn Cys Ala Ala Tyr Thr Ala Val
 50                  55                  60

Asp Asp Ala Glu Thr Asp Glu Ala Ala Ala Leu Leu Asn Ala Glu
 65                  70                  75                  80

Ala Pro Arg Leu Leu Ala Glu Ala Cys Ala Pro His Gly Ala Arg Leu
                 85                  90                  95

Val His Leu Ser Thr Asp Tyr Val Phe Pro Gly Asp Ala Arg Thr Pro
                100                 105                 110

Tyr Ala Glu Asp His Pro Thr Ala Pro Arg Ser Ala Tyr Gly Arg Thr
                115                 120                 125

Lys Arg Asp Gly Glu Gln Ala Val Leu Thr Ala Leu Pro Thr Ala Thr
                130                 135                 140

Val Leu Arg Thr Ala Trp Leu Tyr Gly Arg Thr Gly Arg Ser Phe Val
145                 150                 155                 160

Arg Thr Met Ile Glu Arg Glu Ala Arg Gly Gly Ala Ile Asp Val Val
                165                 170                 175

Ala Asp Gln Arg Gly Gln Pro Thr Trp Thr Gly Asp Leu Ala Asp Arg
                180                 185                 190

Ile Val Ala Val Gly Arg Leu Pro Gly Val His Gly Ile Leu His Ala
                195                 200                 205

Thr Asn Ala Gly Ser Ala Thr Trp Tyr Asp Leu Ala Gln Glu Val Phe
    210                 215                 220

Arg Leu Leu Gly Ala Asp Pro Gly Arg Val Arg Pro Thr Thr Gly Ala
225                 230                 235                 240

Ala Phe Arg Arg Pro Ala Pro Arg Pro Ala Tyr Ser Val Leu Gly His
                245                 250                 255

Asp Arg Trp Arg Gly Thr Gly Leu Val Pro Leu Arg Asp Trp Arg Ser
                260                 265                 270

Ala Leu Arg Glu Ala Phe Pro Asp Ile Leu Ala Ala Glu His Pro Pro
                275                 280                 285

Thr Arg Arg Gly Ala Ala
    290

<210> SEQ ID NO 28
<211> LENGTH: 1008
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
ggatccagcg aaggaggtgc tgagatgaag ctgatcaccg tgctcggtgc gtcgggcttc      60
atcggctcgg ctgtcacgcg tgcactggcg cagcagccaa tccggctgcg agcggtggcg     120
cgcaggcagt tcacgcccgc gcccggccaa gccgagacga ccgtcgtcgc cgctgatctc     180
accgaccgtg tcgcgctcgc cgacgcggtc gcgggatcgg acgcggtcgt gtacctgctt     240
ctgtcagacg gcggatggcg cgcggtcgag accgaggacg ccgaacgcgt gaacgtgggc     300
gtcatgcggg acctcatcga cgtcaccggc agcgacaacg gacgcccccc ggtggtggtg     360
ttcggcggta ccgtctcgca ggtcggtgtg ccacctcggg agccgctcga cggcagcgag     420
cccgacaacc cggcgactcc ctacgacata cagaagctga cagcggaaca gatcctcaag     480
aaggccacgg caaatggcca ggtgcgcggc atcagcctgc gtctgccgac gatattcggt     540
gaaaccacgg cacaaggcgc gaaccacgac cgcggtgtcg tgtcgtccat ggcgcggcga     600
gcgctcgacg gccaggcact caccatctgg ggcgacggca gcgtgcgacg cgacgtcgtc     660
```

```
catgtcgagg acgtcgcggc ggcgttcacc gcggcactgg ccaacccgga ttcccttgtc    720
ggcggccact ggctgatcgg cgcgggccga ggcgatcagc ttggggagat tttccgcctc    780
gtggcacggg aagtggccga gcagaccggg cagcgcccgg tcgaggtgac ctgtgtggaa    840
ccaccgtcgc acgcacctga gatggatttc cgcagcgtca ccatcgattc ctcgccgttc    900
cgggcggtca ccggctggcg cccagagatt tcgctgtccg aaggagtgcg tcgcactgtc    960
gccgcattga cgacatcagt tcatggaaag gctcgcgcat gatctaga              1008
```